(12) United States Patent
Cappola

(10) Patent No.: US 9,445,810 B2
(45) Date of Patent: Sep. 20, 2016

(54) STAPLING DEVICE WITH GRASPING JAW MECHANISM

(71) Applicant: Covidien LP, Mansfield, MA (US)

(72) Inventor: Kenneth M. Cappola, Monroe, CT (US)

(73) Assignee: Covidien LP, Mansfield, MA (US)

( * ) Notice: Subject to any disclaimer, the term of this patent is extended or adjusted under 35 U.S.C. 154(b) by 564 days.

(21) Appl. No.: 13/915,824

(22) Filed: Jun. 12, 2013

(65) Prior Publication Data

US 2014/0367448 A1 Dec. 18, 2014

(51) Int. Cl.
*A61B 17/068* (2006.01)
*A61B 17/072* (2006.01)
*A61B 17/29* (2006.01)
*A61B 17/00* (2006.01)

(52) U.S. Cl.
CPC ....... *A61B 17/068* (2013.01); *A61B 17/07207* (2013.01); *A61B 17/29* (2013.01); *A61B 17/2909* (2013.01); *A61B 2017/00393* (2013.01); *A61B 2017/2923* (2013.01)

(58) Field of Classification Search
None
See application file for complete search history.

(56) References Cited

U.S. PATENT DOCUMENTS

| | | |
|---|---|---|
| 3,079,606 A | 3/1963 | Bobrov et al. |
| 3,490,675 A | 1/1970 | Green et al. |
| 3,499,591 A | 3/1970 | Green |
| 3,777,538 A | 12/1973 | Weatherly et al. |
| 3,882,854 A | 5/1975 | Hulka et al. |
| 4,027,510 A | 6/1977 | Hiltebrandt |
| 4,086,926 A | 5/1978 | Green et al. |
| 4,244,372 A | 1/1981 | Kapitanov et al. |
| 4,429,695 A | 2/1984 | Green |
| 4,471,781 A | 9/1984 | Di Giovanni et al. |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |

(Continued)

FOREIGN PATENT DOCUMENTS

| | | |
|---|---|---|
| AU | 198654765 | 9/1986 |
| DE | 2744824 | 4/1978 |

(Continued)

OTHER PUBLICATIONS

European Search Report dated Nov. 24, 2014 issued in European Application No. 14 17 1910.

*Primary Examiner* — Hemant M Desai
*Assistant Examiner* — Tanzim Imam

(57) ABSTRACT

A surgical device includes a handle assembly, an elongated member, and a tool assembly. The handle assembly includes a mode selection mechanism configured to alternate the surgical device between a grasping mode of operation and a clamping mode of operation. The tool assembly includes a cartridge assembly having a plurality of staples and an anvil assembly. The tool assembly is configured to grasp and release tissue in the grasping mode of operation and configured to clamp and staple tissue in the clamping mode of operation. The mode selection mechanism includes a switch and a pawl. When a moveable handle of the handle assembly is compressed with the switch held in a depressed position, the device is in the grasping mode of operation. When the moveable handle is compressed with the switch in a neutral position, the device is in the clamping mode of operation.

8 Claims, 24 Drawing Sheets

(56) References Cited

U.S. PATENT DOCUMENTS

| | | |
|---|---|---|
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | deSalis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughetti et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,290,299 A | 3/1994 | Fain et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,229 A | 8/1994 | Noda |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,383,881 A | 1/1995 | Green et al. |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,073 A | 4/1995 | Porter |
| 5,407,293 A | 4/1995 | Crainich |
| 5,413,268 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,431,669 A | 7/1995 | Thompson et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,836 A | 9/1995 | Huitema et al. |
| 5,452,837 A | 9/1995 | Williamson, IV et al. |
| 5,456,401 A | 10/1995 | Green et al. |
| 5,464,300 A | 11/1995 | Crainich |
| 5,465,894 A | 11/1995 | Clark et al. |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |

(56) References Cited

U.S. PATENT DOCUMENTS

| | | | |
|---|---|---|---|
| 5,601,224 | A | 2/1997 | Bishop et al. |
| 5,605,272 | A | 2/1997 | Witt et al. |
| 5,607,095 | A | 3/1997 | Smith et al. |
| 5,615,820 | A | 4/1997 | Viola |
| 5,618,291 | A | 4/1997 | Thompson et al. |
| 5,624,452 | A | 4/1997 | Yates |
| 5,626,587 | A | 5/1997 | Bishop et al. |
| 5,628,446 | A | 5/1997 | Geiste et al. |
| 5,630,539 | A | 5/1997 | Plyley et al. |
| 5,630,540 | A | 5/1997 | Blewett |
| 5,630,541 | A | 5/1997 | Williamson, IV et al. |
| 5,632,432 | A | 5/1997 | Schulze et al. |
| 5,634,584 | A | 6/1997 | Okorocha et al. |
| 5,636,780 | A | 6/1997 | Green et al. |
| 5,643,289 | A | 7/1997 | Sauer et al. |
| 5,645,209 | A | 7/1997 | Green et al. |
| 5,647,526 | A | 7/1997 | Green et al. |
| 5,651,491 | A | 7/1997 | Heaton et al. |
| 5,653,373 | A | 8/1997 | Green et al. |
| 5,653,374 | A | 8/1997 | Young et al. |
| 5,653,721 | A | 8/1997 | Knodel et al. |
| 5,655,698 | A | 8/1997 | Yoon |
| 5,657,921 | A | 8/1997 | Young et al. |
| 5,658,300 | A | 8/1997 | Bito et al. |
| 5,662,258 | A | 9/1997 | Knodel et al. |
| 5,662,259 | A | 9/1997 | Yoon |
| 5,662,260 | A | 9/1997 | Yoon |
| 5,662,662 | A | 9/1997 | Bishop et al. |
| 5,662,666 | A | 9/1997 | Onuki et al. |
| 5,665,085 | A | 9/1997 | Nardella |
| 5,667,517 | A | 9/1997 | Hooven |
| 5,669,544 | A | 9/1997 | Schulze et al. |
| 5,673,840 | A | 10/1997 | Schulze et al. |
| 5,673,841 | A | 10/1997 | Schulze et al. |
| 5,673,842 | A | 10/1997 | Bittner et al. |
| 5,676,674 | A | 10/1997 | Bolanos et al. |
| 5,680,981 | A | 10/1997 | Mililli et al. |
| 5,680,982 | A | 10/1997 | Schulze et al. |
| 5,680,983 | A | 10/1997 | Plyley et al. |
| 5,690,269 | A | 11/1997 | Bolanos et al. |
| 5,692,668 | A | 12/1997 | Schulze et al. |
| 5,697,542 | A | 12/1997 | Knodel et al. |
| 5,697,543 | A | 12/1997 | Burdorff |
| 5,702,409 | A | 12/1997 | Rayburn et al. |
| 5,704,534 | A | 1/1998 | Huitema et al. |
| 5,706,997 | A | 1/1998 | Green et al. |
| 5,709,334 | A | 1/1998 | Sorrentino et al. |
| 5,711,472 | A | 1/1998 | Bryan |
| 5,713,505 | A | 2/1998 | Huitema |
| 5,715,988 | A | 2/1998 | Palmer |
| 5,716,366 | A | 2/1998 | Yates |
| 5,718,359 | A | 2/1998 | Palmer |
| 5,725,536 | A | 3/1998 | Oberlin et al. |
| 5,725,554 | A | 3/1998 | Simon et al. |
| 5,728,110 | A | 3/1998 | Vidal et al. |
| 5,732,806 | A | 3/1998 | Foshee et al. |
| 5,735,848 | A | 4/1998 | Yates et al. |
| 5,743,456 | A | 4/1998 | Jones et al. |
| 5,749,893 | A | 5/1998 | Vidal et al. |
| 5,752,644 | A | 5/1998 | Bolanos et al. |
| 5,762,255 | A | 6/1998 | Chrisman et al. |
| 5,762,256 | A | 6/1998 | Mastri et al. |
| 5,769,303 | A | 6/1998 | Knodel et al. |
| 5,769,892 | A | 6/1998 | Kingwell |
| 5,772,099 | A | 6/1998 | Gravener |
| 5,772,673 | A | 6/1998 | Cuny et al. |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A * | 7/1998 | Mastri ............ A61B 17/07207 227/175.3 |
| 5,782,397 | A | 7/1998 | Koukline |
| 5,782,834 | A | 7/1998 | Lucey et al. |
| 5,785,232 | A | 7/1998 | Vidal et al. |
| 5,797,536 | A | 8/1998 | Smith et al. |
| 5,797,537 | A | 8/1998 | Oberlin et al. |
| 5,797,538 | A | 8/1998 | Heaton et al. |
| 5,810,811 | A | 9/1998 | Yates et al. |
| 5,810,855 | A | 9/1998 | Rayburn et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,109 | A | 10/1998 | McGarry et al. |
| 5,820,009 | A | 10/1998 | Melling et al. |
| 5,823,066 | A | 10/1998 | Huitema et al. |
| 5,826,776 | A | 10/1998 | Schulze et al. |
| 5,829,662 | A | 11/1998 | Allen et al. |
| 5,833,695 | A | 11/1998 | Yoon |
| 5,836,147 | A | 11/1998 | Schnipke |
| 5,855,311 | A | 1/1999 | Hamblin et al. |
| 5,862,972 | A | 1/1999 | Green et al. |
| 5,865,361 | A | 2/1999 | Milliman et al. |
| 5,871,135 | A | 2/1999 | Williamson IV et al. |
| 5,873,873 | A | 2/1999 | Smith et al. |
| 5,878,938 | A | 3/1999 | Bittner et al. |
| 5,893,506 | A | 4/1999 | Powell |
| 5,894,979 | A | 4/1999 | Powell |
| 5,897,562 | A | 4/1999 | Bolanos et al. |
| 5,901,895 | A | 5/1999 | Heaton et al. |
| 5,911,352 | A | 6/1999 | Racenet et al. |
| 5,911,353 | A | 6/1999 | Bolanos et al. |
| 5,918,791 | A | 7/1999 | Sorrentino et al. |
| 5,919,198 | A | 7/1999 | Graves, Jr. et al. |
| 5,922,001 | A | 7/1999 | Yoon |
| 5,931,847 | A | 8/1999 | Bittner et al. |
| 5,941,442 | A | 8/1999 | Geiste et al. |
| 5,954,259 | A | 9/1999 | Viola et al. |
| 5,964,774 | A | 10/1999 | McKean et al. |
| 5,980,510 | A | 11/1999 | Tsonton et al. |
| 5,988,479 | A | 11/1999 | Palmer |
| 6,004,335 | A | 12/1999 | Vaitekunas et al. |
| 6,010,054 | A | 1/2000 | Johnson et al. |
| 6,032,849 | A | 3/2000 | Mastri et al. |
| 6,045,560 | A | 4/2000 | McKean et al. |
| 6,063,097 | A | 5/2000 | Oi et al. |
| 6,079,606 | A | 6/2000 | Milliman et al. |
| 6,099,551 | A | 8/2000 | Gabbay |
| 6,109,500 | A | 8/2000 | Alli et al. |
| 6,131,789 | A | 10/2000 | Schulze et al. |
| 6,131,790 | A | 10/2000 | Piraka |
| 6,155,473 | A | 12/2000 | Tompkins et al. |
| 6,197,017 | B1 | 3/2001 | Brock et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,264,086 | B1 | 7/2001 | McGuckin, Jr. |
| 6,264,087 | B1 | 7/2001 | Whitman |
| 6,269,977 | B1 | 8/2001 | Moore |
| 6,279,809 | B1 | 8/2001 | Nicolo |
| 6,315,183 | B1 | 11/2001 | Piraka |
| 6,315,184 | B1 | 11/2001 | Whitman |
| 6,325,810 | B1 | 12/2001 | Hamilton et al. |
| 6,330,965 | B1 | 12/2001 | Milliman et al. |
| 6,391,038 | B2 | 5/2002 | Vargas et al. |
| 6,398,797 | B2 | 6/2002 | Bombard et al. |
| 6,436,097 | B1 | 8/2002 | Nardella |
| 6,439,446 | B1 | 8/2002 | Perry et al. |
| 6,443,973 | B1 | 9/2002 | Whitman |
| 6,463,623 | B2 | 10/2002 | Ahn et al. |
| 6,478,804 | B2 | 11/2002 | Vargas et al. |
| 6,488,196 | B1 | 12/2002 | Fenton, Jr. |
| 6,503,257 | B2 | 1/2003 | Grant et al. |
| 6,505,768 | B2 | 1/2003 | Whitman |
| 6,544,274 | B2 | 4/2003 | Danitz et al. |
| 6,554,844 | B2 | 4/2003 | Lee et al. |
| 6,565,554 | B1 | 5/2003 | Niemeyer |
| 6,587,750 | B2 | 7/2003 | Gerbi et al. |
| 6,592,597 | B2 | 7/2003 | Grant et al. |
| 6,594,552 | B1 | 7/2003 | Nowlin et al. |
| 6,602,252 | B2 | 8/2003 | Mollenauer |
| 6,612,053 | B2 | 9/2003 | Liao |
| 6,619,529 | B2 | 9/2003 | Green et al. |
| D480,808 | S | 10/2003 | Wells et al. |
| 6,644,532 | B2 | 11/2003 | Green et al. |

(56) References Cited

U.S. PATENT DOCUMENTS

| | | |
|---|---|---|
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,743,240 B2 | 6/2004 | Smith et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,805,273 B2 | 10/2004 | Bilotti et al. |
| 6,808,262 B2 | 10/2004 | Chapoy et al. |
| 6,817,509 B2 | 11/2004 | Geiste et al. |
| 6,824,548 B2 | 11/2004 | Smith et al. |
| 6,830,174 B2 | 12/2004 | Hillstead et al. |
| 6,835,199 B2 | 12/2004 | McGuckin, Jr. et al. |
| 6,837,895 B2 | 1/2005 | Mayenberger |
| 6,843,403 B2 | 1/2005 | Whitman |
| 6,843,794 B2 | 1/2005 | Sixto, Jr. et al. |
| RE38,708 E | 3/2005 | Bolanos et al. |
| 6,877,647 B2 | 4/2005 | Ratcliff et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham |
| 6,945,979 B2 | 9/2005 | Kortenbach et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,070,602 B2 | 7/2006 | Smith et al. |
| 7,083,075 B2 | 8/2006 | Swayze et al. |
| 7,090,685 B2 | 8/2006 | Kortenbach et al. |
| 7,097,089 B2 | 8/2006 | Marczyk |
| 7,105,000 B2 | 9/2006 | McBrayer |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,134,587 B2 | 11/2006 | Schwemberger et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,159,750 B2 | 1/2007 | Racenet et al. |
| 7,168,604 B2 | 1/2007 | Milliman |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Gillum et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |

(56) References Cited

U.S. PATENT DOCUMENTS

| | | |
|---|---|---|
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton et al. |
| 7,740,160 B2 | 6/2010 | Viola |
| 7,743,960 B2 | 6/2010 | Whitman |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |

(56) References Cited

U.S. PATENT DOCUMENTS

| | | |
|---|---|---|
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica et al. |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,151 B2 | 4/2012 | Ingmanson et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,558 B2 | 5/2012 | Sapienza |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,236,010 B2 | 8/2012 | Ortiz et al. |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,252,009 B2 | 8/2012 | Weller et al. |
| 8,267,300 B2 | 9/2012 | Boudreaux |
| 8,272,554 B2 | 9/2012 | Whitman et al. |
| 2003/0009193 A1 | 1/2003 | Corsaro |
| 2004/0108357 A1 | 6/2004 | Milliman |
| 2004/0193186 A1 | 9/2004 | Kortenbach et al. |
| 2004/0199180 A1 | 10/2004 | Knodel et al. |
| 2004/0199181 A1 | 10/2004 | Knodel et al. |
| 2004/0232201 A1* | 11/2004 | Wenchell ......... A61B 17/07207 227/176.1 |
| 2004/0243151 A1 | 12/2004 | Demmy |
| 2004/0267310 A1 | 12/2004 | Racenet |
| 2005/0103819 A1 | 5/2005 | Racenet |
| 2005/0119669 A1 | 6/2005 | Demmy |
| 2005/0139636 A1 | 6/2005 | Schwemberger et al. |
| 2005/0143759 A1 | 6/2005 | Kelly |
| 2005/0145672 A1 | 7/2005 | Schwemberger et al. |
| 2005/0189397 A1 | 9/2005 | Jankowski |
| 2005/0216055 A1 | 9/2005 | Scirica et al. |
| 2005/0247752 A1 | 11/2005 | Kelly et al. |
| 2005/0247753 A1 | 11/2005 | Kelly et al. |
| 2006/0049229 A1 | 3/2006 | Milliman et al. |
| 2006/0180634 A1 | 8/2006 | Shelton, IV et al. |
| 2006/0289602 A1 | 12/2006 | Wales et al. |

(56) References Cited

U.S. PATENT DOCUMENTS

| | | |
|---|---|---|
| 2007/0027469 A1 | 2/2007 | Smith et al. |
| 2007/0060952 A1 | 3/2007 | Roby et al. |
| 2007/0073341 A1 | 3/2007 | Smith et al. |
| 2007/0084897 A1 | 4/2007 | Shelton, IV et al. |
| 2007/0084899 A1 | 4/2007 | Taylor |
| 2007/0102472 A1 | 5/2007 | Shelton, IV |
| 2007/0106317 A1 | 5/2007 | Shelton, IV |
| 2007/0119901 A1 | 5/2007 | Ehrenfels et al. |
| 2007/0145096 A1 | 6/2007 | Viola et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0179528 A1 | 8/2007 | Soltz et al. |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078808 A1 | 4/2008 | Hess et al. |
| 2008/0110961 A1 | 5/2008 | Voegele et al. |
| 2008/0149685 A1 | 6/2008 | Smith et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296344 A1 | 12/2008 | Cropper et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314958 A1* | 12/2008 | Scirica ............. A61B 17/07207 227/175.2 |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005808 A1 | 1/2009 | Hess et al. |
| 2009/0065549 A1 | 3/2009 | Viola |
| 2009/0078739 A1 | 3/2009 | Viola |
| 2009/0090763 A1 | 4/2009 | Zemlok et al. |
| 2009/0090766 A1 | 4/2009 | Knodel |
| 2009/0145947 A1* | 6/2009 | Scirica ............. A61B 17/07207 227/175.2 |
| 2009/0206124 A1* | 8/2009 | Hall ................ A61B 17/07207 227/175.1 |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0255974 A1 | 10/2009 | Viola |
| 2009/0272787 A1 | 11/2009 | Scirica |
| 2009/0277946 A1 | 11/2009 | Marczyk |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2010/0012703 A1 | 1/2010 | Calabrese et al. |
| 2010/0012704 A1 | 1/2010 | Tarinelli Racenet et al. |
| 2010/0069942 A1 | 3/2010 | Shelton, IV |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | MA |
| 2011/0036891 A1 | 2/2011 | Zemlok et al. |
| 2011/0036892 A1* | 2/2011 | Marczyk .......... A61B 17/07207 227/176.1 |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czernik et al. |
| 2011/0186614 A1 | 8/2011 | Kasvikis |

(56) References Cited

U.S. PATENT DOCUMENTS

| | | | |
|---|---|---|---|
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |

FOREIGN PATENT DOCUMENTS

| | | |
|---|---|---|
| DE | 2903159 | 1/1980 |
| DE | 3114135 | 10/1982 |
| DE | 4213426 | 10/1992 |
| DE | 4300307 | 7/1994 |
| EP | 0041022 | 12/1981 |
| EP | 0136950 | 4/1985 |
| EP | 0140552 | 5/1985 |
| EP | 0156774 | 10/1985 |
| EP | 0216532 | 4/1987 |
| EP | 0220029 | 4/1987 |
| EP | 0213817 | 11/1987 |
| EP | 0273468 | 7/1988 |
| EP | 0324635 | 7/1989 |
| EP | 0324637 | 7/1989 |
| EP | 0324638 | 7/1989 |
| EP | 0369324 | 5/1990 |
| EP | 0373762 | 6/1990 |
| EP | 0380025 | 8/1990 |
| EP | 0399701 | 11/1990 |
| EP | 0449394 | 10/1991 |
| EP | 0484677 | 5/1992 |
| EP | 0489436 | 6/1992 |
| EP | 0503662 | 9/1992 |
| EP | 0514139 | 11/1992 |
| EP | 0536903 | 4/1993 |
| EP | 0537572 | 4/1993 |
| EP | 0539762 | 5/1993 |
| EP | 0545029 | 6/1993 |
| EP | 0552050 | 7/1993 |
| EP | 0552423 | 7/1993 |
| EP | 0579038 | 1/1994 |
| EP | 0589306 | 3/1994 |
| EP | 0591946 | 4/1994 |
| EP | 0592243 | 4/1994 |
| EP | 0593920 | 4/1994 |
| EP | 0598202 | 5/1994 |
| EP | 0598579 | 5/1994 |
| EP | 0600182 | 6/1994 |
| EP | 0621006 | 10/1994 |
| EP | 0621009 | 10/1994 |
| EP | 0656188 | 6/1995 |
| EP | 0365153 | 8/1995 |
| EP | 0666057 | 8/1995 |
| EP | 0705571 | 4/1996 |
| EP | 0760230 | 3/1997 |
| EP | 1 908 410 | 4/2008 |
| EP | 2583630 A2 | 4/2013 |
| FR | 2542188 | 9/1984 |
| FR | 2660851 | 10/1991 |
| FR | 2681775 | 10/1991 |
| GB | 1352554 | 4/1971 |
| GB | 1452185 | 4/1971 |
| GB | 1452185 | 10/1976 |
| GB | 1555455 | 11/1979 |
| GB | 2048685 | 12/1980 |
| GB | 2070499 | 9/1981 |
| GB | 20700499 | 9/1981 |
| GB | 2141066 | 12/1984 |
| GB | 2165559 | 4/1986 |
| JP | 51-149958 | 6/1975 |
| JP | 51-149985 | 6/1975 |
| JP | 0666057 | 8/1995 |
| JP | 2001-87272 | 4/2001 |
| SU | 659146 | 4/1979 |
| SU | 728848 | 5/1980 |
| SU | 980703 | 12/1982 |
| SU | 990220 | 1/1983 |
| WO | WO 8302247 | 7/1983 |
| WO | WO 89/10094 | 11/1989 |
| WO | WO 9210976 | 7/1992 |
| WO | WO 9308754 | 5/1993 |
| WO | WO 9314706 | 8/1993 |
| WO | WO2004/112618 | 12/2004 |
| WO | WO 2004/112618 | 12/2004 |
| WO | WO2005/037329 | 4/2005 |

* cited by examiner

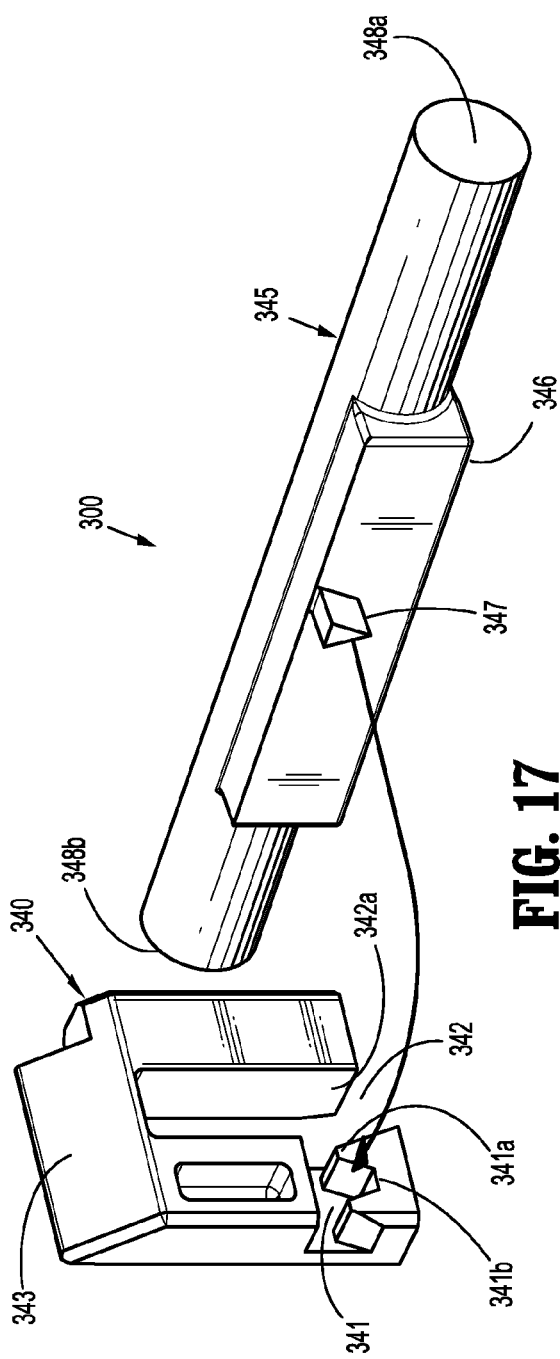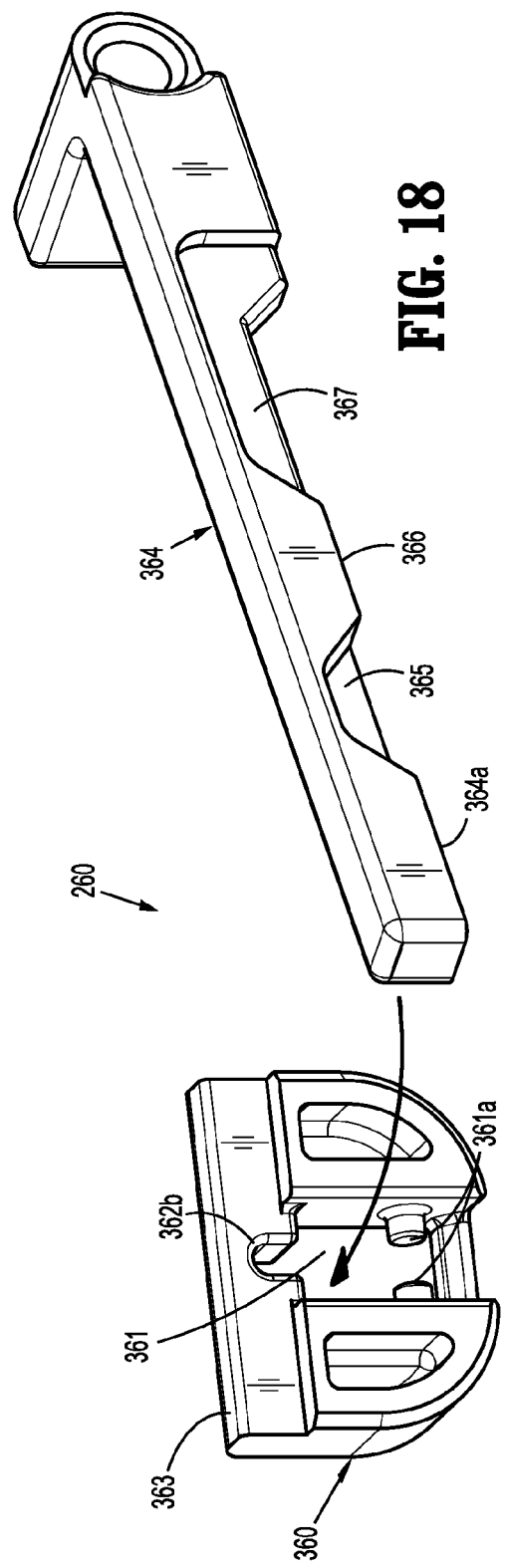

STAPLING DEVICE WITH GRASPING JAW MECHANISM

BACKGROUND

1. Technical Field

The present disclosure relates to a surgical stapling device and, more particularly, to a surgical stapling device configured to operate a tool assembly in a grasping mode.

2. Background of Related Art

Surgical devices wherein tissue is first grasped or clamped between opposing jaw structure and then joined by surgical fasteners are well known in the art. The fasteners are typically in the form of surgical staples, but two-part polymeric fasteners can also be utilized.

Such devices can include a tool assembly with a pair of jaws which are used to capture or clamp tissue. Typically, one of the jaws carries a staple cartridge which houses a plurality of staples arranged, for example, in at least two lateral rows while the other jaw supports an anvil that defines a surface for forming the staple legs as the staples are driven from the staple cartridge. The stapling operation may be effected by cam bars that travel longitudinally through the staple cartridge and act on staple pushers for sequentially ejecting the staples from the staple cartridge. The stapling device can include a knife which travels between the staple rows for longitudinally cutting the stapled tissue between the rows of staples. Known staplers are disclosed in U.S. Pat. Nos. 6,250,532 and 6,241,139, each of which are currently owned by Tyco Healthcare Group LP, and are hereby incorporated herein by reference in its entirety.

In endoscopic or laparoscopic procedures (hereinafter "endoscopic procedures"), surgery is performed through small incisions or through small diameter cannulas inserted through small entrance wounds in the skin. Thus, access to the surgical site is limited. During an endoscopic procedure, it is often necessary to manipulate tissue to properly position the tissue between the jaws of the surgical device. Typically, a grasper is inserted through a cannula to facilitate manipulation of tissue at the surgical site. The need for an additional instrument, i.e., a grasper, requires removal of the stapling device from a cannula or the use of an additional cannula. It would be advantageous to provide a stapling device which can also function as a grasper.

Accordingly, a continuing need exists for an endoscopic or laparoscopic surgical device having a tool assembly which can be quickly and easily manipulated between different firing and grasping modes of operation.

SUMMARY

In accordance with the present disclosure, a surgical stapling device is provided which includes a handle assembly having a movable handle, an elongated member, and a tool assembly. The tool assembly may be part of a Loading Unit or LU. The tool assembly is positioned at a distal end of the elongated member and includes an anvil assembly and a cartridge assembly. The anvil assembly and the cartridge assembly are movable in relation to each other between open and closed positions. The elongated member extends distally from the handle assembly defining a longitudinal axis.

The handle assembly includes an actuation shaft and a mode selection mechanism which alternates the stapling device between a grasping mode and a clamping mode. In the grasping mode, the anvil assembly and the cartridge assembly are moveable between the open and the closed positions. In the clamping mode, the anvil assembly and the cartridge assembly are locked in the closed position and the stapling device may fire staples from the cartridge assembly. In embodiments, the stapling device has an initial condition such that the anvil assembly and the cartridge assembly are locked in the open position and the actuation shaft is prevented from distal advancement.

The mode selection mechanism includes a mode selection switch operatively associated with a mode pawl. The mode selection switch has a neutral position and a depressed position. In the neutral position the mode selection switch permits the mode pawl to engage the actuation shaft and in the depressed position the mode selection switch at least partially inhibits the mode pawl from engaging the actuation shaft.

In aspects of the disclosure, the stapling device is in the grasping mode of operation when the actuation shaft is distally advanced with the mode selection switch in the depressed position and the stapling device is in the clamping mode of operation when the actuation shaft is distally advanced with the mode selection switch in the neutral position. In embodiments, once the stapling device is in the clamping mode of operation the mode selection switch no longer transitions the stapling device to the grasping mode of operation. In some embodiments, the mode pawl prevents the stapling device from transitioning to the grasping mode of operation from the clamping mode of operation by preventing proximal retraction of the actuation shaft. The mode pawl may prevent proximal retraction of the actuation shaft when the mode pawl is at least partially inhibited from engaging the actuation shaft by the mode selection switch.

In some aspects of the disclosure, the mode selection assembly includes a switch biasing member. The switch biasing member urging the mode selection switch towards the neutral position. In embodiments, the mode selection switch includes a wall retaining the mode selection switch in the depressed position against the switch biasing member.

In another aspect of the disclosure, the mode selection mechanism further includes a locking assembly. The locking assembly having a lock pawl and a disconnect link operatively associated with the moveable handle. The lock pawl is positioned distal to the mode pawl and includes a central slot with a camming protrusion. The camming protrusion is configured to engage a portion of the disconnect link. The disconnect link is received within the central slot and includes a distal recess, a cam portion, and a proximal recess. The locking assembly has a first position, a second position, and a third position. In the first position, the camming protrusion engages the disconnect link in the distal recess. In the second position, the camming protrusion engages the disconnect link on the cam portion. In the third position, the camming protrusion engages the disconnect link in the proximal recess. In the initial condition the locking assembly is in the first position such that the lock pawl engages the actuation shaft preventing advancement of the actuation shaft. When the moveable handle is compressed from the initial non-compressed position with the mode selection switch in the depressed position, the stapling device is in the first mode of operation. When the moveable handle is compressed from the initial non-compressed position with the mode selection switch in the neutral position, the stapling device is in the second mode of operation.

In particular aspects of the disclosure, in the first mode of operation, the distal end of the actuation shaft is proximal to the mode pawl.

In yet another aspect of the disclosure, a method for using a surgical stapling device is disclosed. The method includes the steps of providing a surgical stapling device, opening a tool assembly of the surgical stapling device, and clamping tissue within the tool assembly. The surgical stapling device provided in the method may include any of the surgical stapling devices disclosed herein. The method may include the step of manipulating the tissue with the tool assembly before the step of grasping. The method may also include the step of firing staples through the tissue after the step of clamping. The method may further include the step of releasing the tissue after the step of clamping.

BRIEF DESCRIPTION OF THE DRAWINGS

Embodiments of the presently disclosed surgical stapling device are disclosed herein with reference to the drawings wherein:

FIG. 17 is an enlarged view of the switch and switch pawl of FIG. 16;

FIG. 18 is an enlarged view of the lock pawl and disconnect link of FIG. 16;

DETAILED DESCRIPTION OF THE EMBODIMENTS

Figure 1:
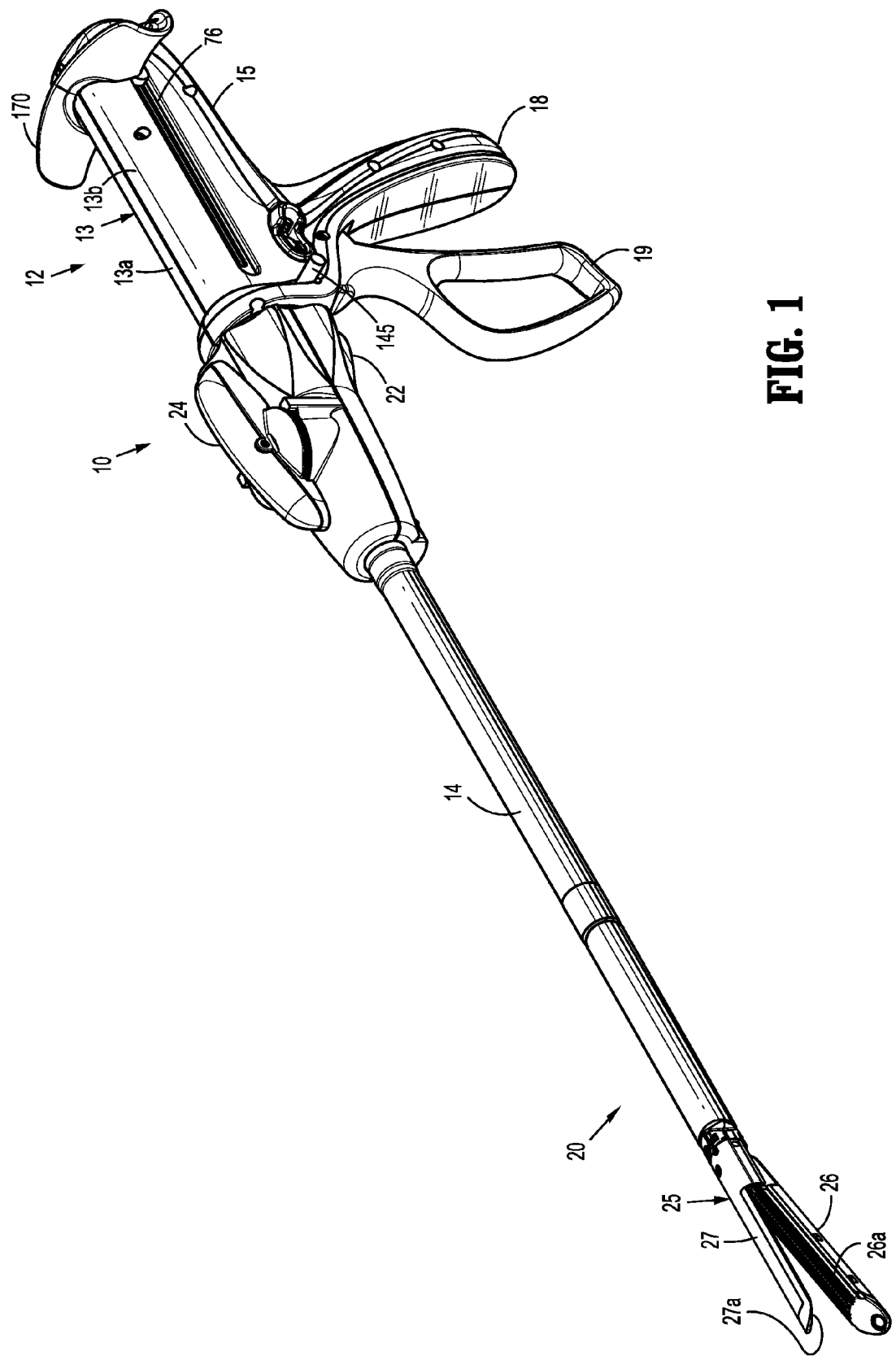
FIG. 1 is a side perspective view of the presently disclosed surgical stapling device.

Embodiments of the presently disclosed grasping jaw mechanism will now be described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" will refer to the portion of the device closest to the clinician and the term "distal" will refer to the portion of the device furthest from the clinician.

FIG. 1 illustrates an embodiment of a presently disclosed surgical stapling device 10. Device 10 includes a handle assembly 12, an elongated member 14 extending distally from handle assembly 12 defining a longitudinal axis, and a tool assembly 25 supported on a distal end of the elongated member 14. Tool assembly 25 can be part of a loading unit ("LU") 20 which is releasably secured to a distal end of elongated member 14 and includes a proximal body portion 24, which forms an extension of elongated member 14, and a tool assembly 25. Tool assembly 25 is supported on a distal end of proximal body 24 and includes a first jaw 26 supporting a cartridge assembly 26a and a second jaw 27 supporting an anvil assembly 27a. In an embodiment, tool assembly 25 is pivotally connected to body portion 24 about an axis substantially perpendicular to the longitudinal axis of elongated member 14.

Cartridge assembly 26a houses a plurality of staples and is movable in relation to anvil assembly 27a between an open position spaced from anvil assembly 27a and an approximated or closed position in juxtaposed alignment with anvil assembly 27a. Tool assembly 25 may be arranged such that cartridge assembly 26a is moveable and anvil assembly 27a is stationary (as shown) or, alternatively, such that anvil assembly 27a is movable and cartridge assembly 26a is stationary or such that both the anvil assembly 27a and the cartridge assembly 26a are movable. In an embodiment, tool assembly 25 is configured to apply linear rows of staples measuring from about 30 mm to about 60 mm in length. Tool assemblies having linear rows of staples of other lengths and/or different staple array configurations are also envisioned. In embodiments, cartridge assembly 26a can be removably supported on first jaw 26 to facilitate reuse of stapling device 10 without replacement of LU 20 and/or where stapling device 10 does not include a LU 20.

Handle assembly 12 includes a housing 13 having a barrel portion 15 and a stationary handle 18. A movable handle 19 is pivotally supported on housing 13 adjacent stationary handle 18. In an embodiment, housing 13 is formed from molded half-sections 13a, 13b which are joined together by ultrasonic welding, adhesives, mechanical fasteners, or the like. A rotation control member 22 is rotatably mounted at the forward end of barrel portion 19 to facilitate rotation of elongated member 14 with respect to handle assembly 12. Rotation control member 22 also can be formed from molded plastic half-sections, although other materials, e.g., metals, and manufacturing methods are envisioned. An articulation lever 24 can also be mounted on the forward end of barrel portion 19 adjacent rotation control member 22 to facilitate articulation of tool assembly 25. U.S. Pat. No. 5,865,361 to Milliman et al. (the "'361 patent") and U.S. Pat. No. 7,967,178 to Scirica et al. (the "'178 patent"), describe a rotation control assembly and articulation assembly for a surgical stapling apparatus each of which is currently owned by Tyco Healthcare Group LP and is hereby incorporated herein by reference in its entirety.

Figure 2:
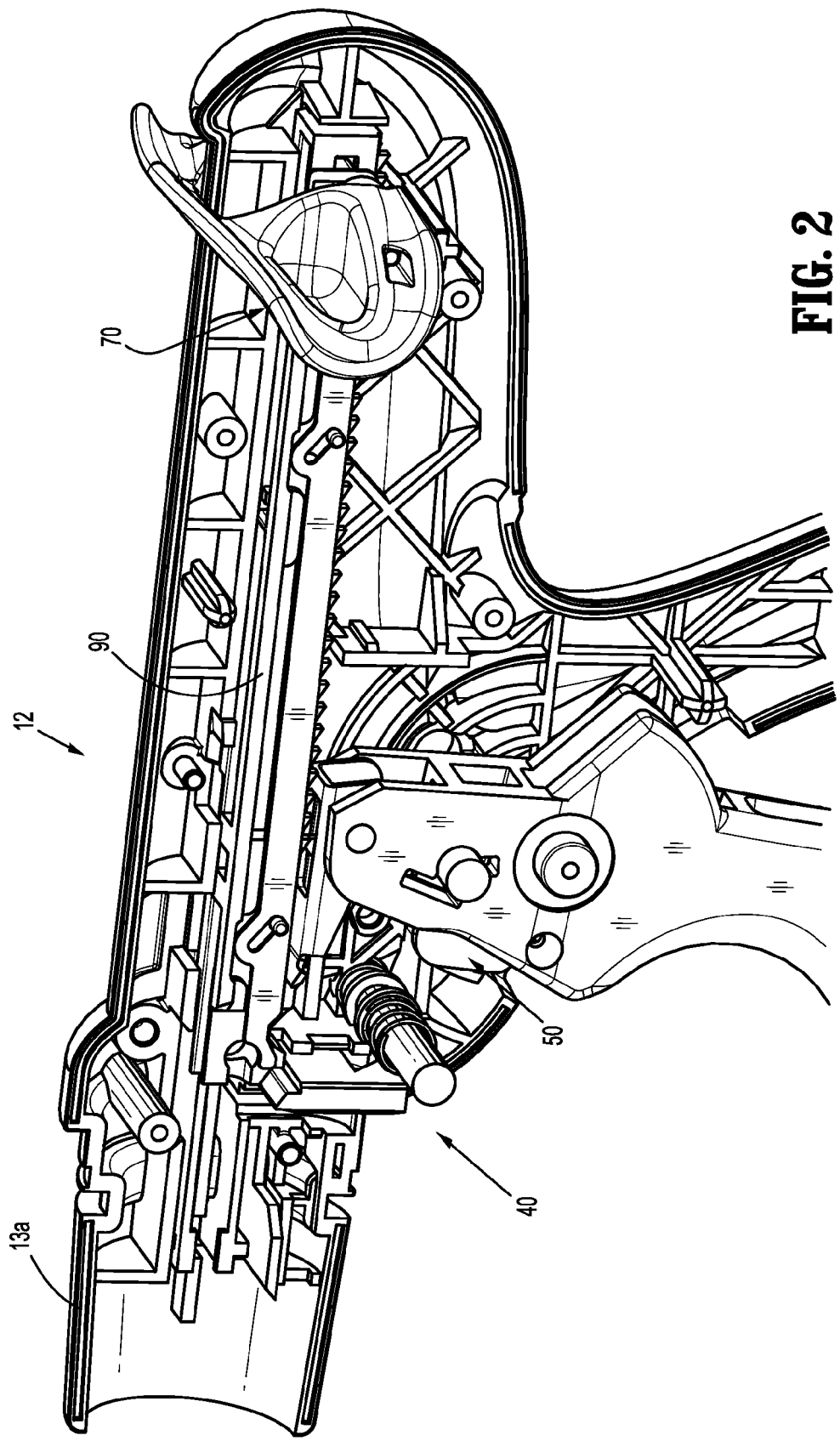
FIG. 2 is a side perspective of the handle assembly of the stapling device of FIG. 1 with a housing half-section removed including one embodiment of a mode selection assembly.
Figure 3:
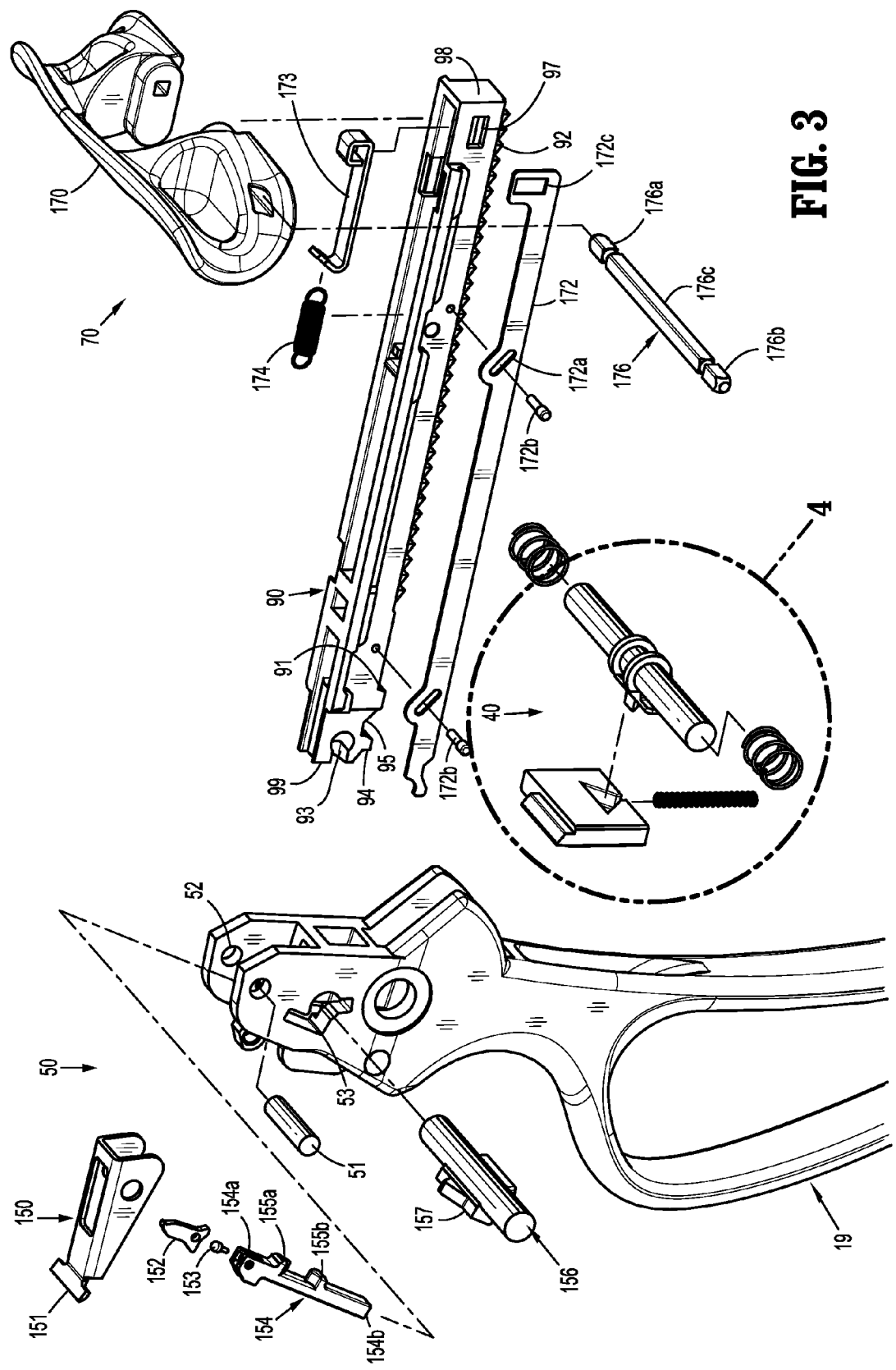
FIG. 3 is a side perspective view of the internal components of the handle assembly of the surgical stapling device shown in FIG. 1, with parts separated.
Figure 12:
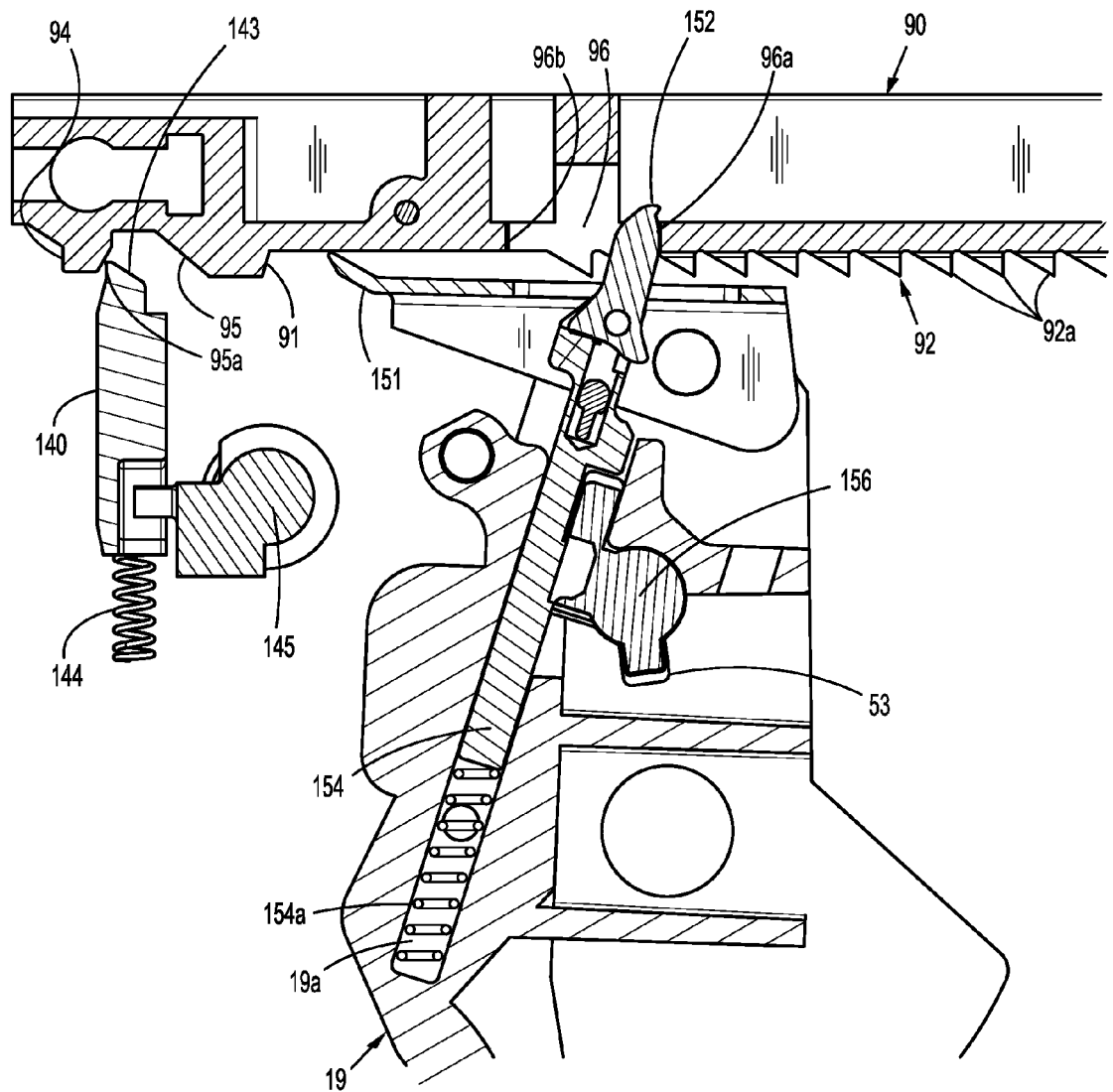
FIG. 12 is a side cross-sectional view taken along the longitudinal axis of the handle assembly with the device in the grasping mode.

Referring now to FIGS. 2 and 3, handle assembly 12 includes a mode selection assembly 40, an actuation assembly 50, a retraction assembly 70, and an actuation member or actuation shaft 90. As shown in FIG. 3, actuation shaft 90 includes a shoulder 91, a toothed rack 92, a distal recess 93, a distal surface or detent 94, a distal cutout 95, and a grasping slot 96 (FIG. 12). Actuation shaft 90 is disposed along the longitudinal axis of elongated member 14 and supports toothed rack 92 to facilitate distal advancement of actuation shaft 90 as described in detail below. Distal recess 93 is configured to receive the proximal end of a control rod (not shown) that is operably associated with tool assembly 25 and can be advanced in the manner discussed in the '361 patent to clamp tissue and eject staples from the cartridge assembly 26a.

Figure 4:
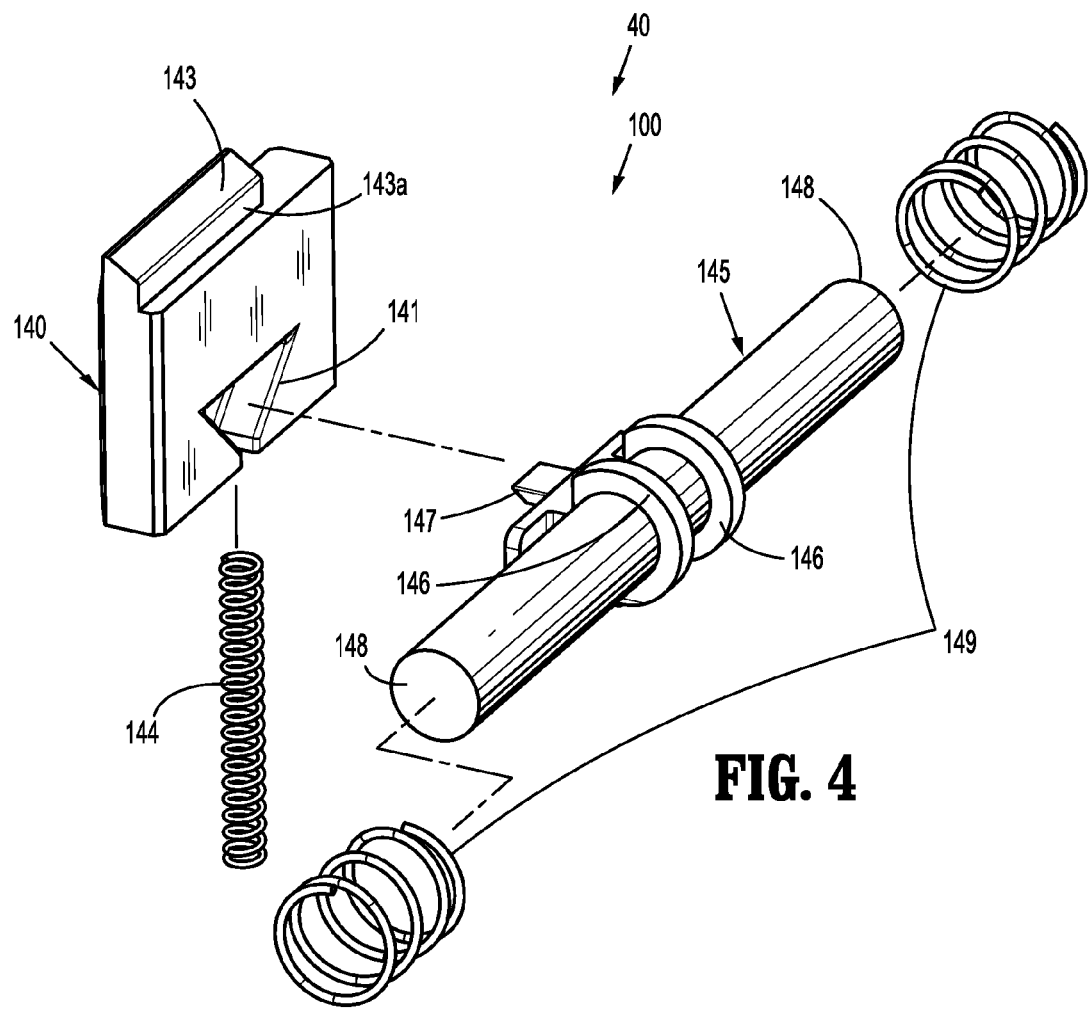
FIG. 4 is an enlarged view of the indicated area of detail shown in FIG. 3.
Figure 5:
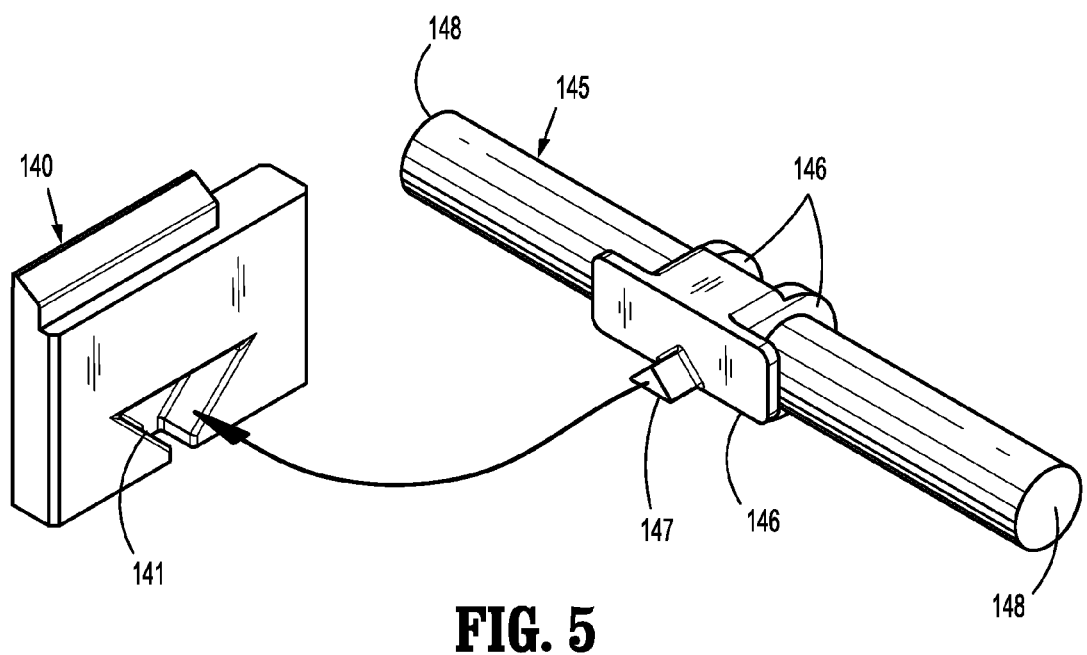
FIG. 5 is a perspective view of the switch and switch pawl shown in FIG. 4.
Figure 6:
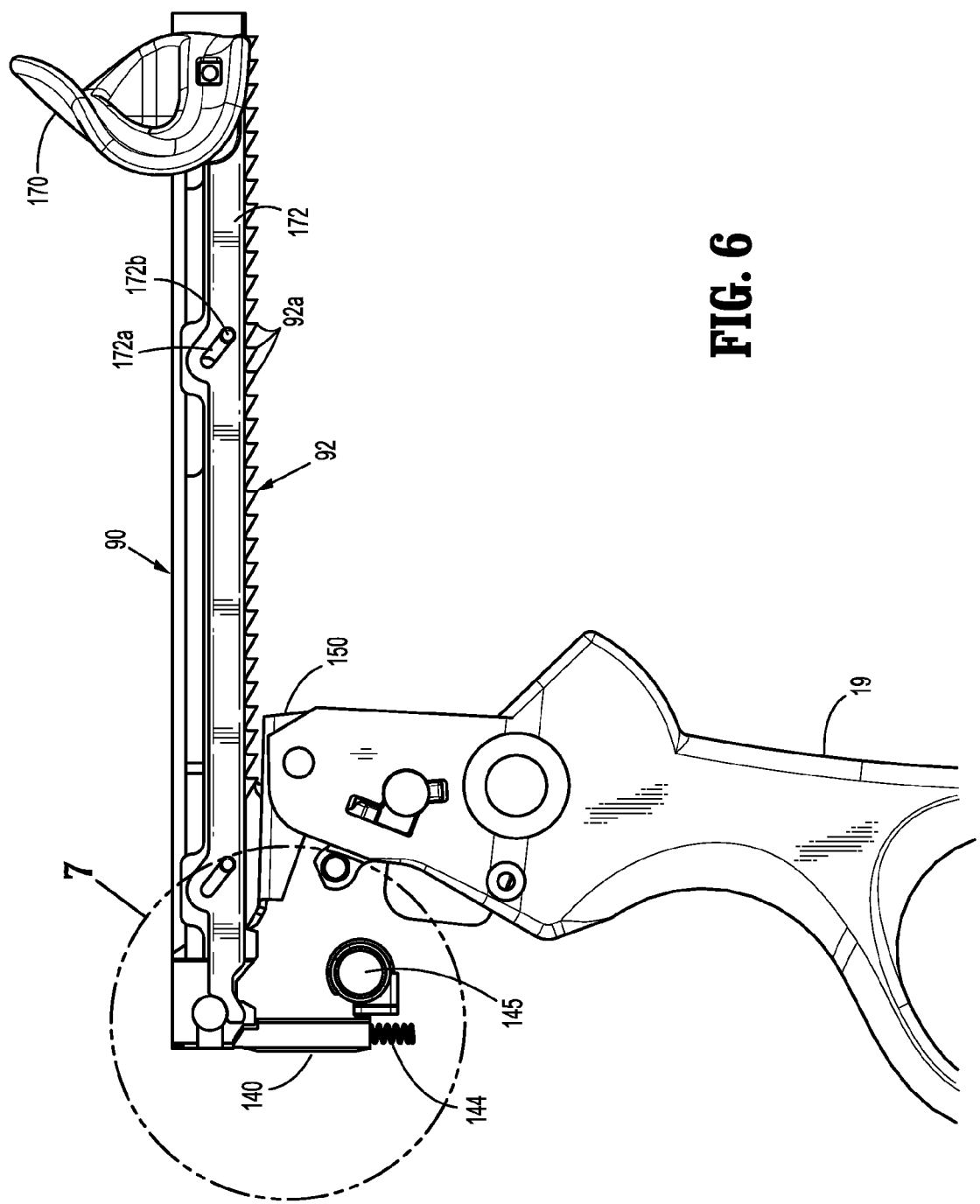
FIG. 6 is a side view of internal components of the handle assembly including an actuation shaft with the rack in a refracted position.
Figure 7:
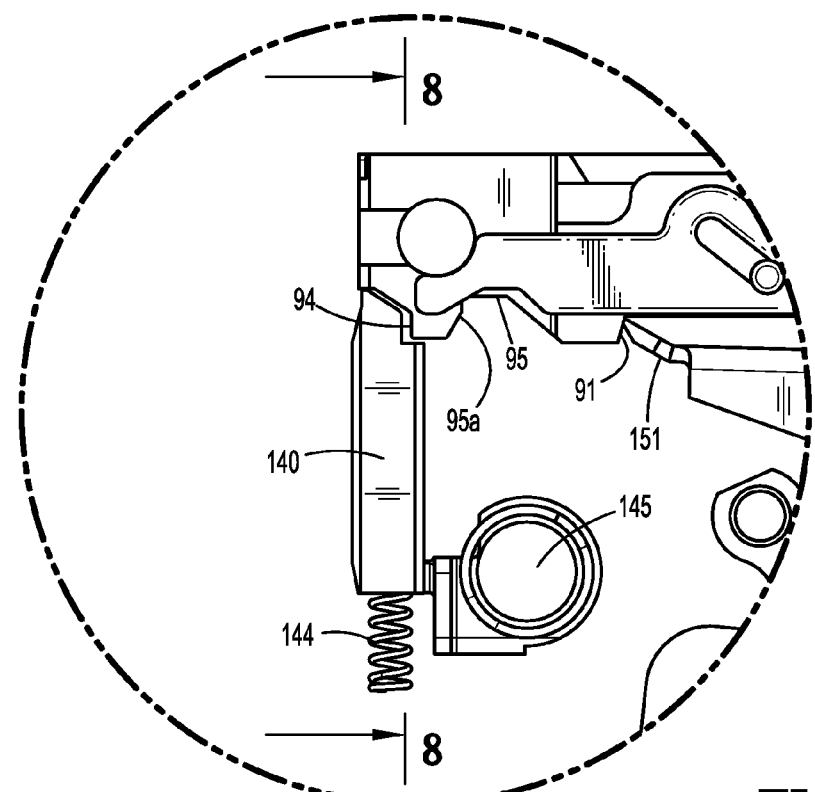
FIG. 7 is an enlarged view of the indicated area of detail shown in FIG. 6.

With reference also to FIGS. 4 and 5, mode selection assembly 40 includes switch assembly 100 having a vertical or switch pawl 140, a vertical or switch pawl biasing member 144, a switch 145, and switch biasing members 149. As shown, switch pawl 140 is substantially rectangular with a triangular detent receiving slot 141 in a proximally facing surface of switch pawl 140. Switch pawl biasing member 144 is supported by housing 13 at a position to urge a camming surface 143 of switch pawl 140 into engagement with actuation shaft 90. Alternatively, other switch pawl configurations are envisioned.

As shown, switch 145 is generally cylindrical and is slidably received through openings (not shown) in housing 13. Switch 145 is supported substantially orthogonal to the longitudinal axis of elongated member 14 as shown in FIG. 1 and includes raised portions 146 and a protrusion or detent 147. Detent 147 is received within detent receiving slot 141 of switch pawl 140 as will be discussed in further detail below. Switch 145 has ends 148 disposed outside of housing 13 which are accessible to a clinician. Switch biasing members 149 are disposed over a portion of switch 145 between raised portion 146 and housing 13 to urge switch 145 to a centrally located position within housing 13.

Figure 8:
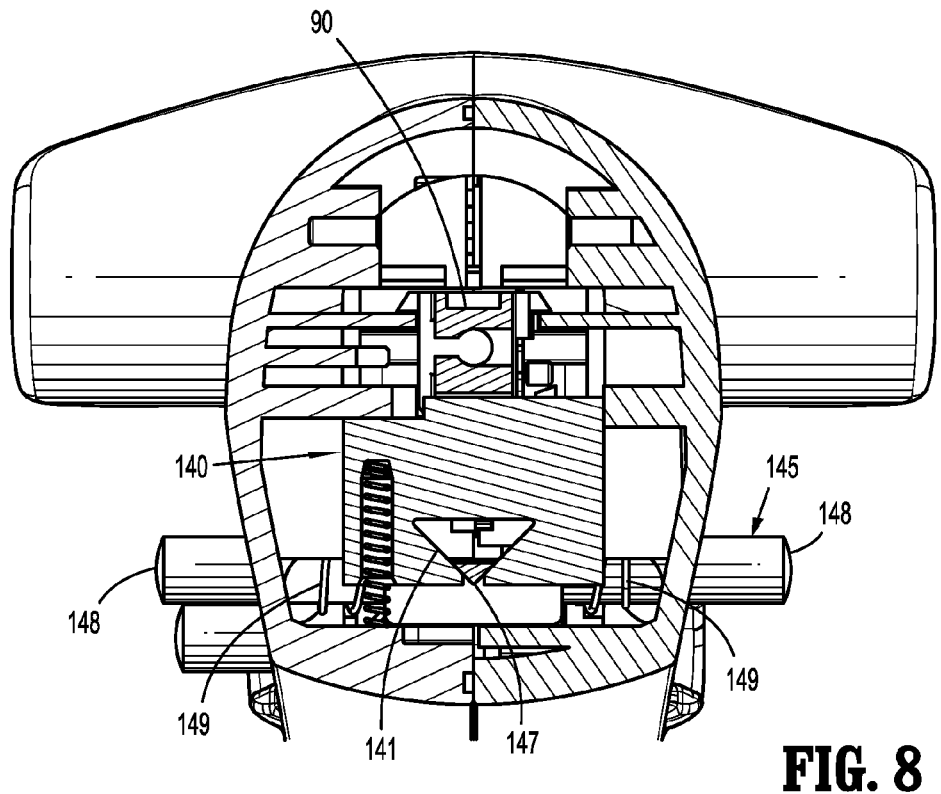
FIG. 8 is a cross-sectional view taken along the section lines 8-8 of FIG. 7 with the switch in a neutral position.
Figure 9:
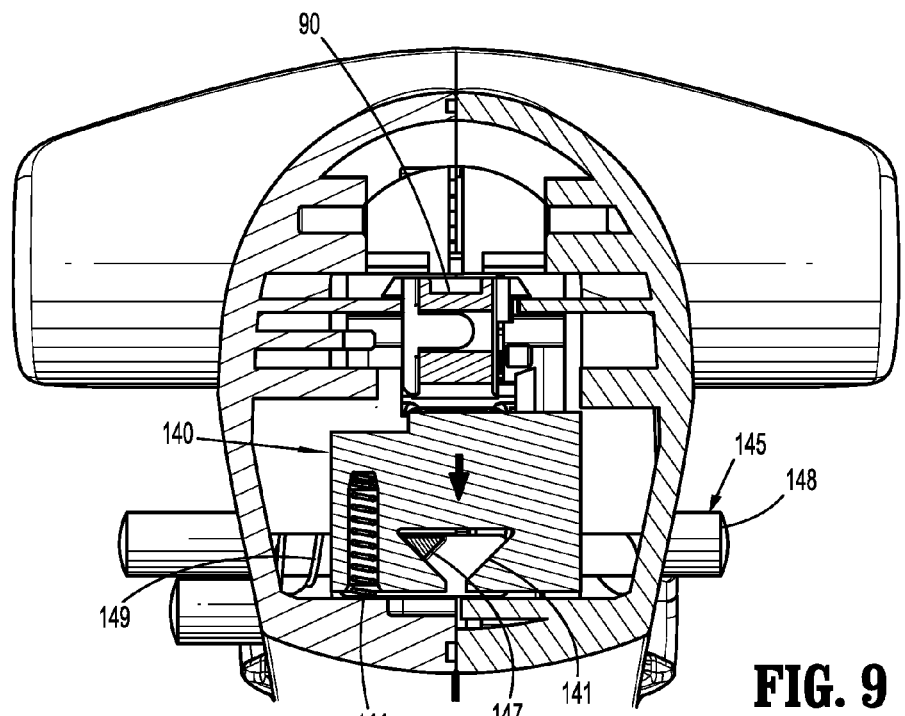
FIG. 9 is a cross-sectional view taken along the section lines 8-8 of FIG. 7 with the switch in a depressed position.
Figure 10:
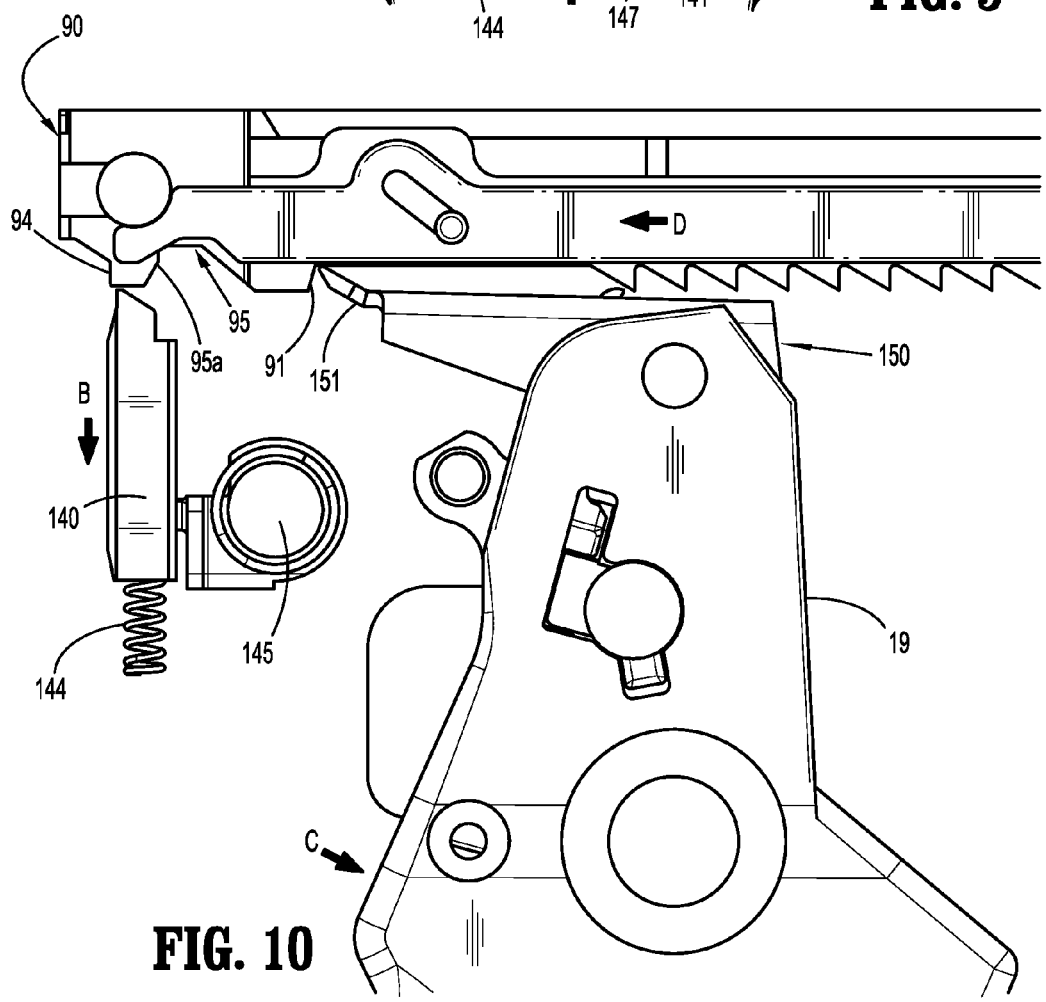
FIG. 10 is a side view of the internal components of the handle assembly with the switch pawl cammed down out of engagement with the actuation shaft.

Referring to FIGS. 6-10, switch 145 has a neutral position (FIG. 8) and a depressed position (FIG. 9). In the neutral position of switch 145, switch biasing members 149 urge switch 145 such that detent 147 is positioned centrally within detent receiving slot 141 of switch pawl 140 to allow switch pawl biasing member 144 to urge switch pawl 140 upwardly into engagement with actuation shaft 90 as shown in FIG. 8. In the depressed position of switch 145, detent 147 of switch 145 is in engagement with the wall defining detent receiving slot 141 to retain switch pawl 140 out of engagement with actuation shaft 90 against the urging of switch pawl biasing member 144 as shown in FIGS. 9 and 10. It will be appreciated that either end of switch 145 may be depressed to transition switch 145 from the neutral position to the depressed position.

Referring back to FIG. 3, actuation assembly 50 includes an actuation pawl 150, a grasping pawl 152, an actuation arm 154, and an actuation button 156. The '178 patent incorporated by reference herein describes a similar actuation assembly for a surgical stapling apparatus. Actuation pawl 150 includes a distal finger 151 for engaging toothed rack 92 of actuation shaft 90 and is pivotally supported about a pivot member 51 on an upper end of movable handle 19. Grasping pawl 152 is pivotally supported within a slot formed in an end 154a of actuation arm 154. A grasping pawl biasing member 153 is positioned to urge grasping pawl 152 in a counter-clockwise direction, as viewed in FIG. 3, to allow grasping pawl 152 to ratchet or slide over toothed rack 92 of actuation shaft 90. Actuation arm 154 is disposed within a recess 19a in movable handle 19 as shown in FIG. 12.

Figure 11:
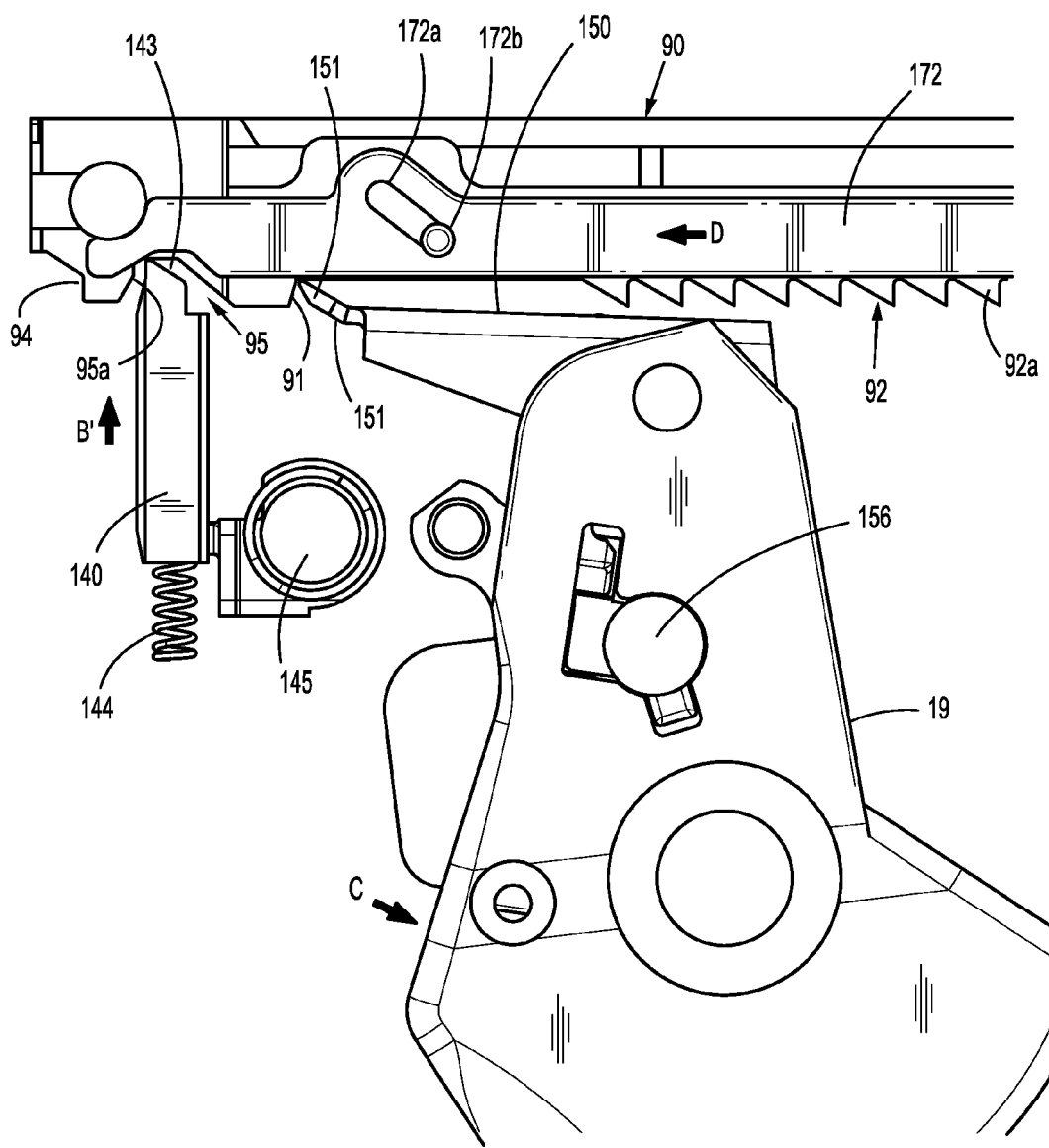
FIG. 11 is a side view of the internal components of the handle assembly in the clamping mode.
Figure 12A:
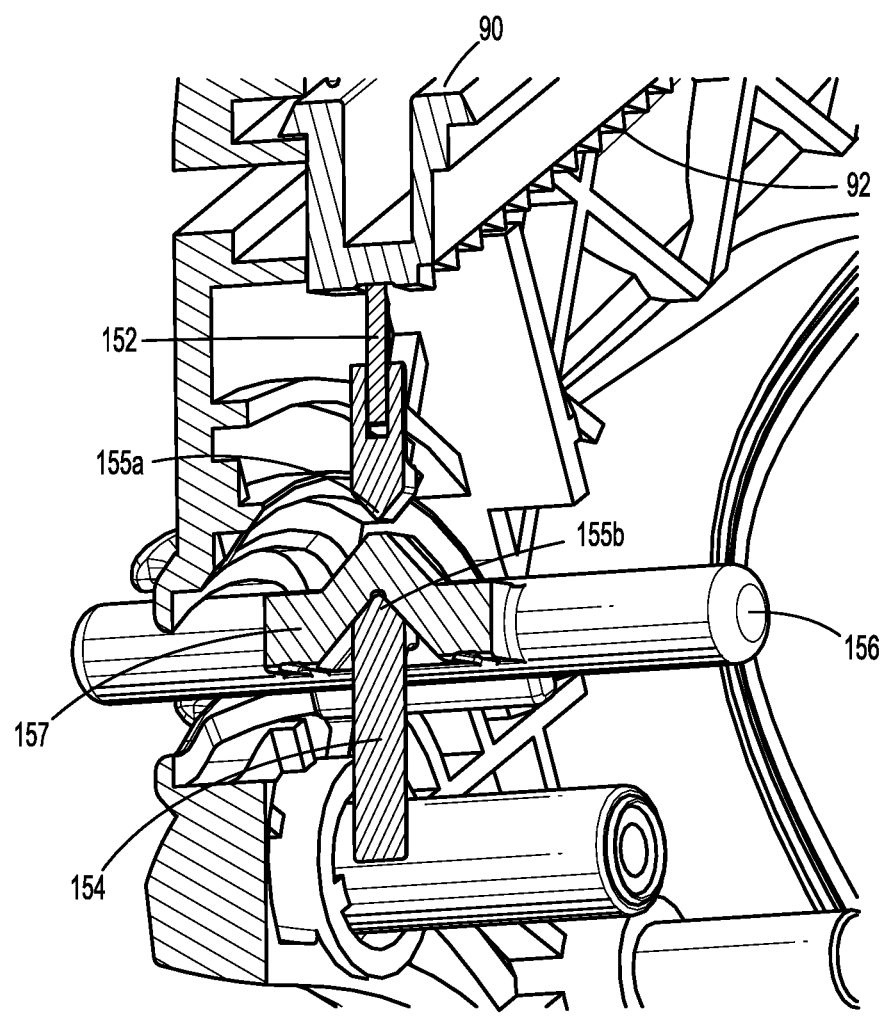
FIG. 12A is a front view of the internal components of the handle assembly with the actuation button in the centered position.
Figure 12B:
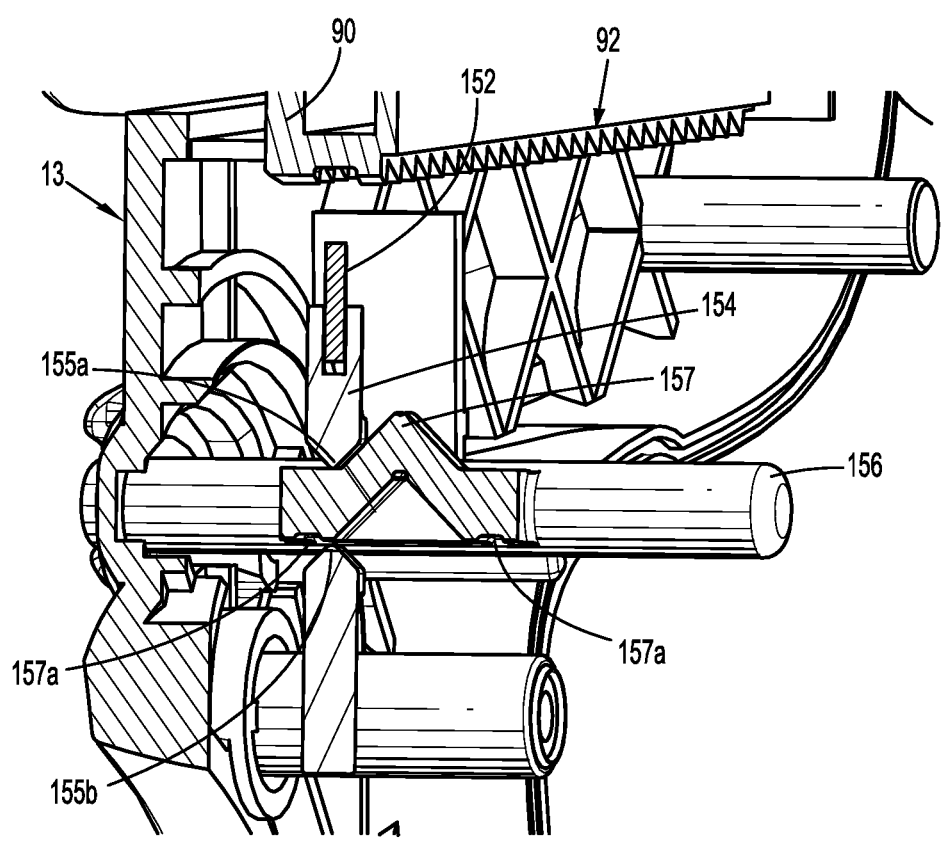
FIG. 12B is a front view of the internal components of the handle assembly with the actuation button in the off-centered position.

With reference to FIGS. 11-12B, actuation arm 154 is moveable between an extended position (FIG. 12A) and a retracted position (FIG. 12B). In embodiments, actuation assembly 50 includes an actuation arm biasing member 154a positioned within recess 19a to urge actuation arm 154 towards the extended position. In the extended position, the grasping pawl 152 of actuation arm 154 is received within the grasping slot 96 of the actuation shaft 90. In the retracted position, grasping pawl 152 is positioned beneath grasping slot 96.

Referring also to FIG. 3, actuation button 156 is slidably positioned through a bore 53 formed in movable handle 19 as shown in FIG. 12. Bore 53 is positioned substantially orthogonally to recess 19a within movable handle 19 such that an actuation button cam 157 of actuation button 156 is slidably positioned between upper and lower cam surfaces 155a, 155b of actuation arm 154. Actuation cam member 157 is engaged with or positioned to engage the upper and lower cam surfaces 155a, 155b such that lateral movement of actuation button 156 transitions actuation arm 154 between the extended position and the retracted position. Actuation cam member 157 may include notches 157a (FIG. 12B) to retain actuation arm 156 in the retracted position.

Referring to FIG. 12A, with the actuation button 156 in its centered position, actuation arm 154 is positioned in the extended position by engagement of actuation cam member 157 with upper cam surface 155a of actuation arm 154. When actuation arm 154 is in its extended position, grasping pawl 152 extends into grasping slot 96 (FIG. 12) formed in actuation shaft 90. When movable handle 19 is compressed, actuation pawl 150 engages shoulder 91 on actuation shaft 90 to advance the actuation shaft 90 distally to advance the control rod (not shown) which moves the jaws of the tool assembly to the closed position. When moveable handle 19 is returned to its non-compressed position, by a handle biasing member (not shown) and/or manually by the clinician, grasping pawl 152 engages the proximal surface 96a (FIG. 12) defining a proximal end of slot 96 to retain movable handle in an intermediate position between the non-compressed and compressed positions. In embodiments where a handle biasing member is associated with moveable handle 19, it is noted that the handle biasing member is a light spring which cannot move actuation shaft 90 proximally because of friction associated with the components of tool assembly 25 (FIG. 1) driven by actuation shaft 90. However, a clinician can manipulate movable handle 19 to move actuation shaft 90 and, thus, move tool assembly 25 (FIG. 1) between the open position and the closed position. As long as the clinician depresses switch 145, switch pawl 140 is retained out of engagement with actuation shaft 90 to facilitate retraction of actuation shaft 90. In embodiments, movable handle 19 is prevented from moving to the non-compressed position by engagement of grasping pawl 152 with proximal surface 96a of grasping slot 96. This prevents actuation pawl 150 from moving to a position to engage toothed rack 92 of actuation shaft 90 in the grasping mode.

Referring to FIG. 12B, when movable handle 19 is moved to the compressed position and actuation button 156 is depressed from the centered position to the off-center position, v-shaped cam member 157 engages cam surface 155b on actuation arm 154 to retract actuation arm 154 within recess 19a (FIG. 12) of movable handle 19 and retract grasping pawl 152 to a position below actuation shaft 90. In embodiments, when grasping pawl 152 is positioned below actuation shaft 90, the handle biasing member returns movable handle 19 to its non-compressed position (FIG. 1). When moveable handle 19 returns to its non-compressed position and switch 145 is in the neutral position, switch pawl 140 is moved by switch pawl biasing member 144 into engagement with distal cutout 95 in actuation shaft 90 to prevent proximal retraction of actuation shaft 90. In this position, when moveable handle 19 moves to the non-compressed position, the actuation pawl 150 is positioned to engage toothed rack 92 of actuation shaft 90. Thus, when movable handle 19 is again compressed, actuation pawl 150 engages toothed rack 92 of actuation shaft 90 to distally advance actuation shaft 90 to effect firing of the tool assembly 25. As actuation shaft 90 is distally advanced in the clamping mode, switch pawl 140 ratchets or slides over toothed rack 92 of shaft 90. In the "clamping mode", tissue is clamped and the rack is advanced to fire staples.

With reference again to FIG. 3 and also to FIG. 12, a retraction assembly 70 which includes a retraction handle 170 is connected to the proximal end of actuation shaft 90 by a coupling rod 176. Coupling rod 176 includes right and left engagement portions 176a and 176b for receiving retraction handle 170 and a central portion 176c which is dimensioned and configured to translate within a pair of longitudinal slots 97 formed in actuation shaft 90 adjacent the proximal end thereof. A release plate 172 is operatively associated with actuation shaft 90 and is mounted for movement with respect thereto in response to manipulation of retraction handle 170. A pair of spaced apart pins 172b extend outwardly from a lateral face of actuation shaft 90 and are received by a pair of corresponding angled cam slots 172a formed in release plate 170. Upon proximal movement of retraction handle 170, pins 172b cam release plate 172 downwardly with respect to actuation shaft 90 and with respect to toothed rack 92 such that the bottom portion of release plate 172 extends below toothed rack 92 to disengage finger 151 of actuation pawl 150 and switch pawl 140 from toothed rack 92 as indicated by the dashed line in FIG. 13. A transverse slot 172c is formed at the proximal end of release plate 172 to accommodate the central portion 176c of coupling rod 176 and elongated slots 76 (FIG. 1) are defined in the barrel portion 15 of handle 13 to accommodate the longitudinal translation of coupling rod 90 as retraction handle 170 is pulled proximally to retract actuation shaft 90 and thus retract the control rod (not shown). Coupling rod 176 is biased distally in relation to actuation shaft 90 by retraction biasing member 174 which is secured at one end to coupling rod 176 via connector 173 and at the other end to a portion of actuation shaft 90. A similar retraction device is disclosed in U.S. Pat. No. 6,330,965 and the '178 patent, each of which is currently owned by Tyco Healthcare Group LP and is incorporated herein by reference in its entirety In an initial condition of device 10 illustrated in FIGS. 6-8, moveable handle 19 is in the pre-actuated or non-compressed position, tool assembly 25 is in the open position (FIG. 1), the assemblies 40, 50, 70 of device 10 are each in the biased positions, and actuation shaft 90 is prevented from distally advancing. More specifically, switch 145 is biased to the neutral position to permit switch pawl 140 to engage distal surface 94 of actuation shaft 90 to prevent advancement of actuation shaft 90 and actuation button 156 is biased to the centered position such that the actuation arm 154 is in the extended position such that grasping pawl 152 is received within grasping slot 96.

Referring to FIGS. 9-11, when a clinician depresses switch 145 switch pawl 140 is cammed by detent 147 of switch 145 such that switch pawl 140 is disengaged from distal surface 94 of actuation shaft 90 to permit advancement of actuation shaft 90 as shown in FIG. 9. As the clinician compresses movable handle 19 from an initial non-compressed position towards stationary handle 18, finger 151 of actuation pawl 150 engages shoulder 91 of actuation shaft 90 to distally advance actuation shaft 90 as shown in FIG. 10. Distal advancement of actuation shaft 90 transitions tool assembly 25 to the closed position. Once actuation shaft 90 moves distally such that switch pawl 140 is positioned proximal to distal surface 94 of actuation shaft 90, actuation shaft 90 is prevented from returning to the retracted position without the clinician actuating retraction assembly 70 (FIG. 3) as discussed below.

With reference to FIG. 12, in the grasping mode, switch pawl 140 is maintained in a retracted position by manually depressing switch 145. As discussed above, actuation arm 154 is normally urged to the extended position by actuation button 156 such that grasping pawl 152 of actuation arm 154 extends within grasping slot 96 of actuation shaft 90 between a proximal surface 96a and a distal surface 96b. In the grasping mode, cycling of moveable handle 19 toward and away from stationary handle 18 causes proximal retraction and distal advancement of actuation shaft 90 and correspondingly transitions tool assembly 25 between the open and closed positions. To maintain device 10 in the grasping mode, switch 145 must be held in the depressed position such that actuation shaft 90 is permitted to proximally retract and distally advance as desired by the clinician. As discussed above, in the depressed position switch 145 moves switch pawl 140 against switch pawl biasing member 144 out of engagement with actuation shaft 90. In some embodiments, a distal portion 95a (FIG. 12) of distal cutout 95 is chamfered and engages camming surface 143 of switch pawl 140 when the switch pawl 140 is retracted such that movement of the actuation shaft 90 urges switch pawl 140 toward the retracted position.

In the grasping mode, the clinician is free to open and close the jaws 26, 27 (FIG. 1) of the tool assembly 25 to grasp and release tissue. This allows the clinician to manipulate, grasp, and release tissue as needed to position device 10 in relation to tissue. When tissue is properly positioned within the tool assembly 25, the clinician may release switch 145 and transition device 10 to the clamping mode. In the clamping mode, the clinician may desire keep the tissue clamped within tool assembly 25 and fire staples from first jaw or cartridge assembly 26 through the tissue as described below. A clinician may also release the tissue from within tool assembly 25 by actuation refraction assembly 70 as discussed below. The benefit of the switch pawl 140 is that the switch pawl 140 is always biased toward engagement, ensuring that the actuation shaft 90 cannot be moved proximally. The switch pawl 140 must be disengaged by the user through manipulation of the switch 145, and held in place, in order to utilize the grasper mode.

Referring to FIG. 11, when the clinician releases switch 145, switch pawl 140 moves into distal cutout 95 and engages distal portion 95a of distal cutout 95 to prevent proximal retraction of actuation shaft 90 such that the jaws 26, 27 of tool assembly 25 remain in a clamped or closed position. Device 10 may also be in clamping mode without entering grasping mode if the clinician depresses switch 145 to release actuation shaft 90 and then releases switch 145 when distal surface 94 of actuation shaft 90 is advanced beyond switch pawl 140, i.e., when the movable handle 19 is compressed.

Figure 13:
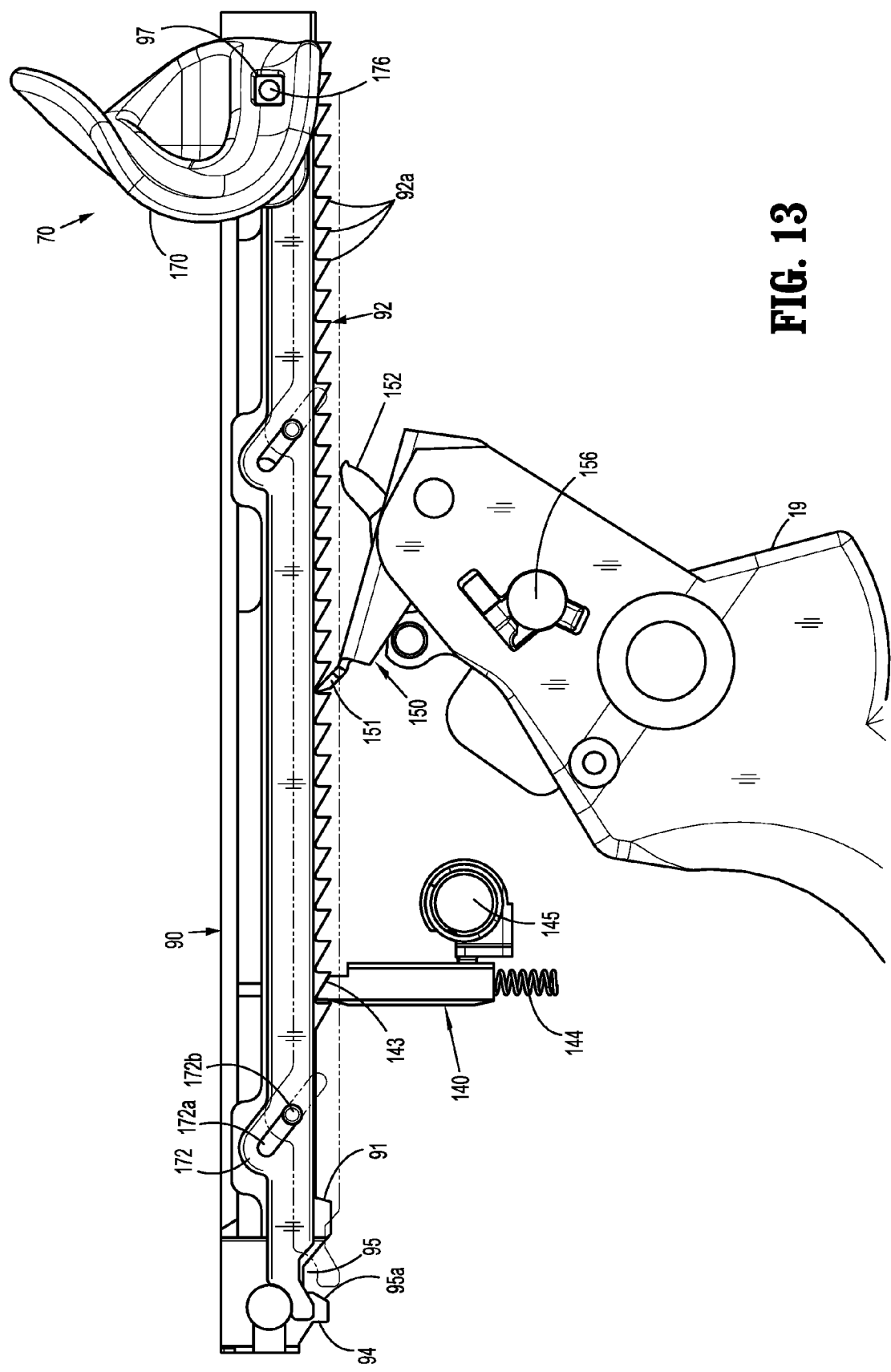
FIG. 13 is a side view of the internal components of the handle assembly in the clamping mode with the actuation shaft partially advanced.

Now referring to FIG. 13, to fire staples from cartridge assembly 26 (FIG. 1), movable handle 19 is returned to the non-compressed position. In some embodiments, actuation button 156 must be depressed to withdraw grasping pawl 152 from grasping slot 96 of actuation arm to permit moveable handle 19 to return to the non-compressed position. The actuation button does not always have to be compressed. The actuation button releases the pawl 152 from rack slot 96 and subsequently disengages the grasper mode (when in the fire mode), and it allows full trigger 19 proximal motion. When the pawl 152 is engaged with rack slot 96, the trigger 19 has limited proximal motion (when in the grasper mode). When switch pawl 140 is engaged with cutout 95 and movable handle 19 is compressed from the non-compressed position towards stationary handle 18, finger 151 of actuation pawl 150 engages a portion of toothed rack 92 of actuation shaft 90 advancing actuation shaft 90 distally. As actuation shaft 90 advances, camming surface 143 of switch pawl 140 passes over cutout 95, shoulder 91, and teeth 92a of toothed rack 92 of actuation shaft 90, such that switch pawl 140 sequentially engages teeth 92a to prevent proximal retraction of actuation shaft 90 when actuation pawl 150 is disengaged from rack 92. In embodiments, once device 10 is in the clamping mode, switch pawl 140 prevents proximal retraction of actuation shaft 90 regardless of the position of switch 145. The pawl 140 is spring loaded upwardly and has a wedge shape to allow distal rack motion and to lock proximal rack motion. Cycling of moveable handle 19 continues to advance actuation shaft 90 and fire staples from cartridge assembly 26.

After the clinician fires the staples or desires to release the tissue from tool assembly 25, the clinician engages retraction assembly 70 by pulling retraction handle 170 proximally. When retraction handle 170 is pulled proximally, coupling rod 176 moves from its distal position towards its proximal position to cam release plate 172 downwardly below toothed rack 92 as discussed above. When retraction plate 172 extends below toothed rack 92, retraction plate 172 disengages finger 151 of actuation pawl 150 and switch pawl 140 from actuation shaft 90. Proximal movement of retraction handle 170 retracts actuation shaft 90 and thus retracts the control rod (not shown) to transition tool assembly 25 from the closed position to the open position and release the tissue from within tool assembly 25. Continued retraction of the control rod returns device 10 to the initial condition. When retraction handle 170 is released, retraction biasing member 144 returns coupling rod 176 to the distal position and moves retraction plate 172 above toothed rack 92 allowing device 10 to be reused.

FIGS. 14-18 illustrate a surgical stapling device 210 including an alternative embodiment of the presently disclosed mode selection assembly 240. Although not illustrated in FIGS. 14-18, device 210 includes an elongated member which extends distally from a handle assembly 212, and a tool assembly which may be supported on the distal end of the elongated member or form part of a DLU as discussed above. The elongated member and the DLU or tool assembly of stapling device 210 are substantially as described above with respect to elongated member 14 and DLU 20 or tool assembly 25 of stapling device 10 (FIG. 1) and will not be described in further detail herein. Handle assembly 212 also includes a stationary handle 218 and a movable handle 219 which is rotatably supported between half-sections 213a, 213b of handle assembly housing 213 as discussed above with respect to moveable handle 19 of stapling device 10 (FIG. 1). A light spring or biasing member may urge movable handle 219 away from stationary handle 218 from a compressed position towards a non-compressed position.

Figure 14:
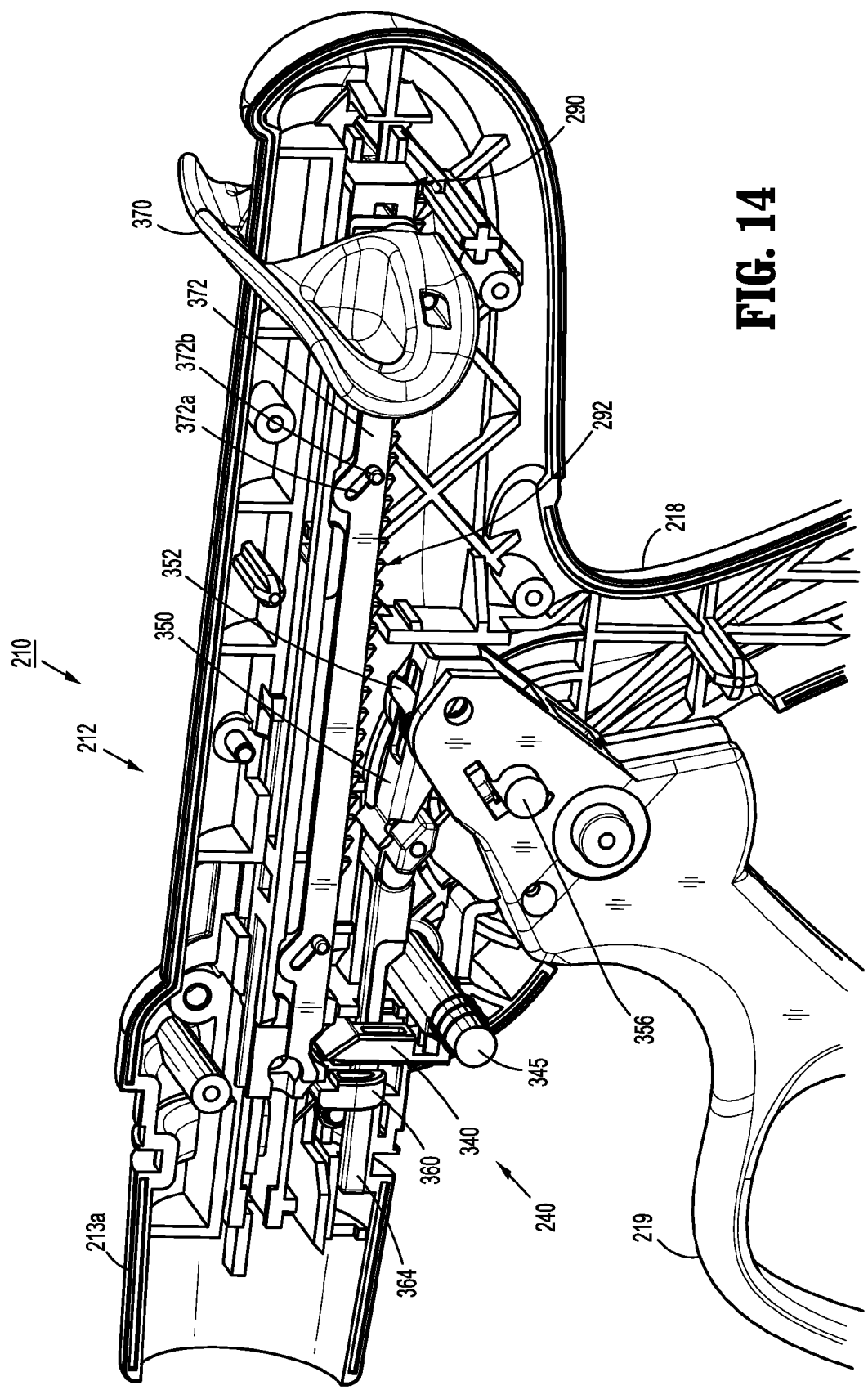
FIG. 14 is a side perspective of the handle assembly of the stapling device of FIG. 1 with a housing half-section removed including another embodiment of the presently disclosed mode selection assembly.
Figure 15:
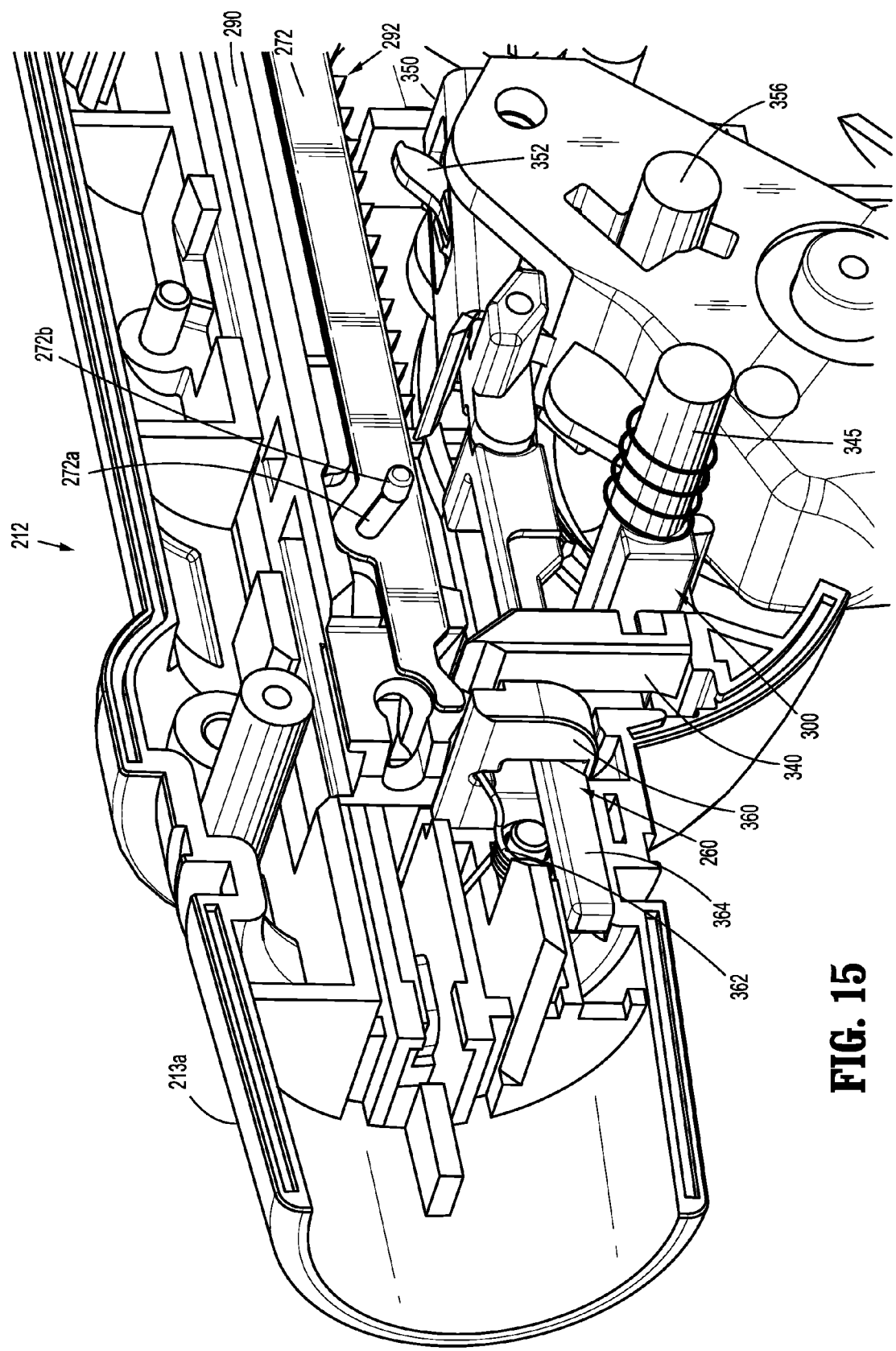
FIG. 15 is a front perspective view of the handle assembly of FIG. 14 with a housing half-section removed in the initial condition.
Figure 16:
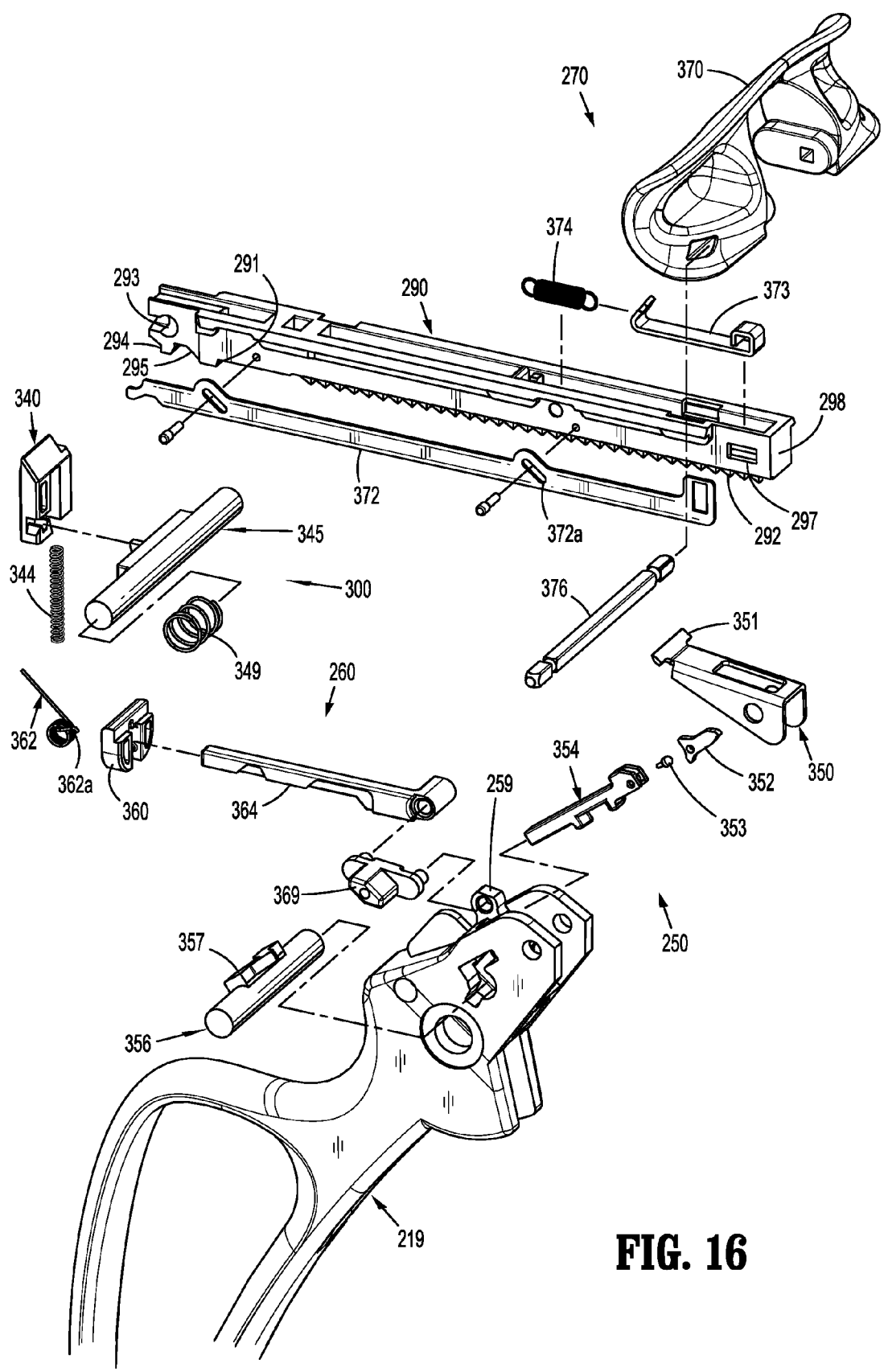
FIG. 16 is a side perspective view of the internal components handle assembly of the surgical stapling device shown in FIG. 14, with parts separated.

Referring to FIGS. 14-16, an actuation pawl 350 is pivotally supported about a pivot member (not shown) and urged towards a toothed rack 292 of an actuation shaft 290 by an actuation pawl biasing member (not shown). Actuation shaft 290 is substantially identical to actuation shaft 90 (FIG. 3) of surgical device 10 (FIG. 1) and will only be described in further detail as it relates to the description of mode selection assembly 240. Handle assembly 212 also includes an actuation assembly 250 and a refraction assembly 270 which are similar to actuation assembly 50 and retraction assembly 70 (FIG. 3) of stapling device 10 and will only be described in further detail as it relates to the description of mode selection assembly 240. Handle assembly 212 further includes a switch assembly 300 which is similar to switch assembly 100 (FIG. 3) of stapling device 10 and only the differences will be discussed in detail herein. More specifically, switch assembly 300 includes a switch pawl 340, a switch pawl biasing member 344, a switch 345, and a switch biasing member 349.

Referring now to FIGS. 16 and 17, switch pawl 340 includes a camming surface 343, a detent receiving slot 341, and a neutral slot 342. Switch pawl biasing member 344 is supported within housing 213 and urges camming surface 343 of switch pawl 340 into engagement with actuation shaft 290. Switch 345 includes a central raised portion 346, a detent 347 positioned on the raised portion, a first switch end 348a, and a second switch end 348b. Switch 345 is positioned substantially orthogonal to the longitudinal axis of housing 213 and is received within a through opening (not shown) in housing 213. Switch biasing member 349 is received over first switch end 348a between raised portion 346 of switch 345 and half-section 213a of housing 213. Switch biasing member 349 urges detent 347 towards a slot wall 342a of neutral slot 342 and urges second end 348b to protrude from half-section 213b.

Figure 22:
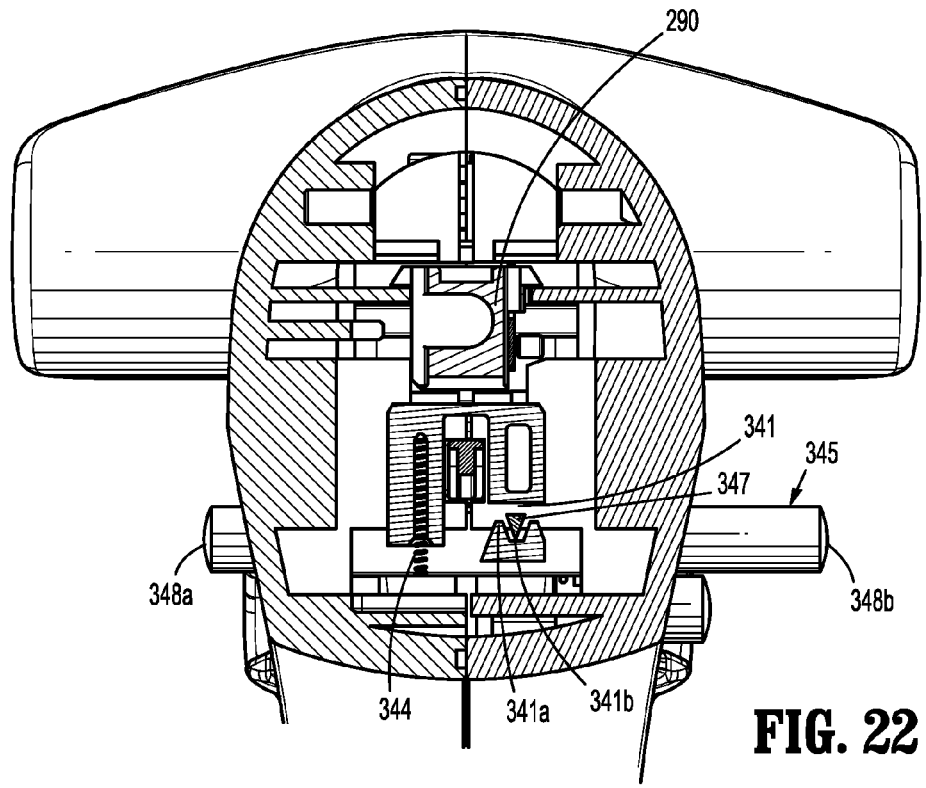
FIG. 22 is a front cross-sectional view taken along the section lines 22-22 of FIG. 20.
Figure 27:
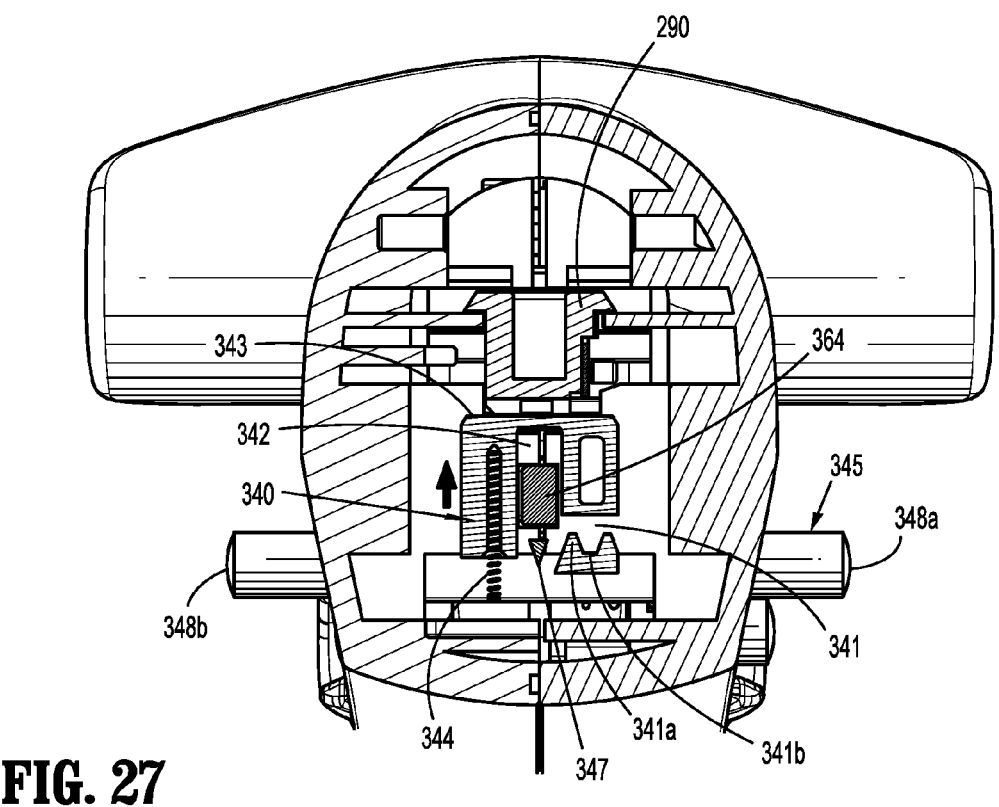
FIG. 27 is a front cross-sectional view taken along the line 27-27 of FIG. 26.

Switch 345 has a neutral position and a depressed position. In the neutral position, detent 347 is positioned within neutral slot 342 and switch pawl 340 is permitted to engage actuation shaft 90 as illustrated in FIG. 27. In embodiments, detent 347 abuts slot wall 342a in the neutral position. In the depressed position, switch 345 is depressed against the switch biasing member 349 and detent 347 is positioned within detent receiving slot 341 as illustrated in FIG. 22. When detent 347 is within detent receiving slot 341, switch pawl 340 is moved against switch pawl biasing member 344 downwardly out of engagement with actuation shaft 290. In embodiments, detent receiving slot 341 includes a wall 341a. When switch 345 is depressed, detent 347 engages wall 341a to move switch pawl 340 downwardly against switch pawl biasing member 344. In some embodiments, when detent 347 passes wall 341a as shown in FIG. 22, switch pawl biasing member 344 may urge a landing 341b into engagement with detent 347 such that landing 341b maintains switch pawl 340 against switch pawl biasing member 344 and prevents switch 345 from returning to the neutral position. There is a switch button 345 and a green button 356. This allows the user to decide when the proximal rack motion lockout is active (potentially limiting use to thick tissue applications and reducing use time in thinner tissue thickness ranges).

Figure 23:
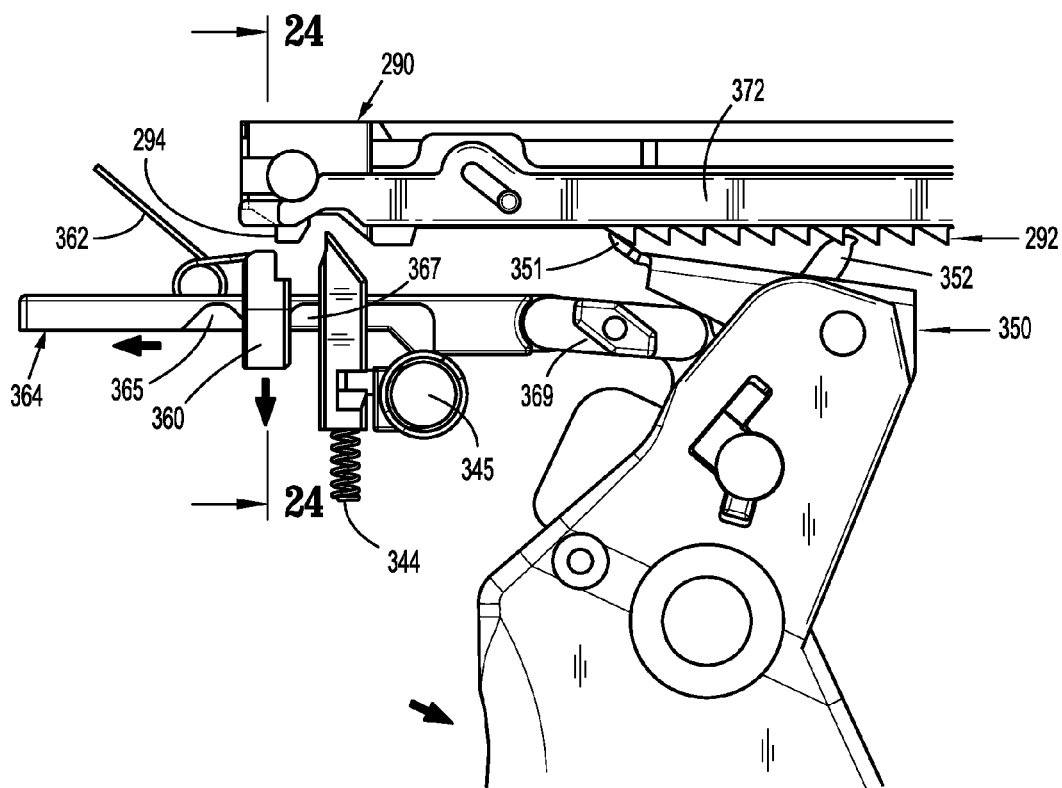
FIG. 23 is a side view of the internal components of the device of FIG. 14 between the initial condition and the grasping mode.

With reference to FIGS. 16 and 18, mode selection assembly 240 also includes a locking assembly 260 having a vertical or lock pawl 360, a vertical or lock pawl biasing member 362, a disconnect link 364, and a proximal link 369. Lock pawl biasing member 362 is supported within housing 213 and urges lock pawl 360 towards actuation shaft 290. In embodiments, a leg 362a of lock pawl biasing member 362 engages a notch 362b (FIG. 18) in lock pawl 360. Lock pawl 360 is positioned distally within housing 213 with respect to switch pawl 340 and includes a locking surface 363 and a central slot 361. Central slot 361 has a camming protrusion 361a and is dimensioned to slidably receive disconnect link 364. Disconnect link 364 has a surface 364a including a distal recess 365, a proximal recess 367, and a disconnect cam 366 positioned between the distal and proximal recesses 365, 367. Lock pawl biasing member 362 urges camming protrusion 361a towards engagement with surface 364a of distal link 364. In embodiments, disconnect link 364 passes through neutral slot 342 of switch pawl 340. A proximal end of disconnect link 364 is operatively associated with a distal end of proximal link 369 (FIG. 23). A proximal end of proximal link 369 is operatively associated with a boss 259 (FIG. 16) formed on moveable handle 219.

Figure 20:
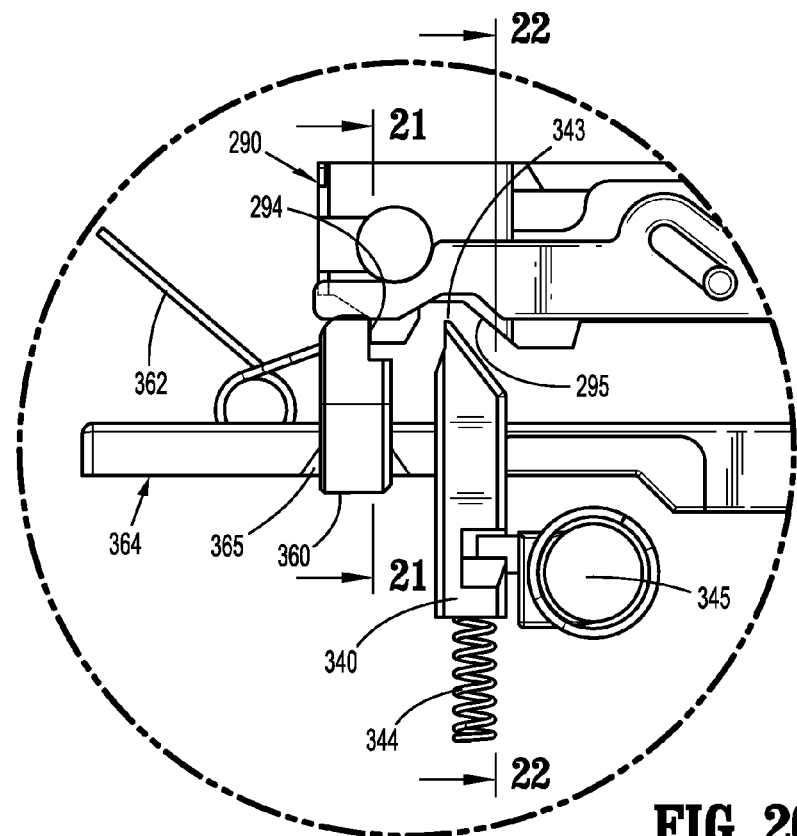
FIG. 20 is an enlarged view of the indicated area of detail shown in FIG. 19.
Figure 21:
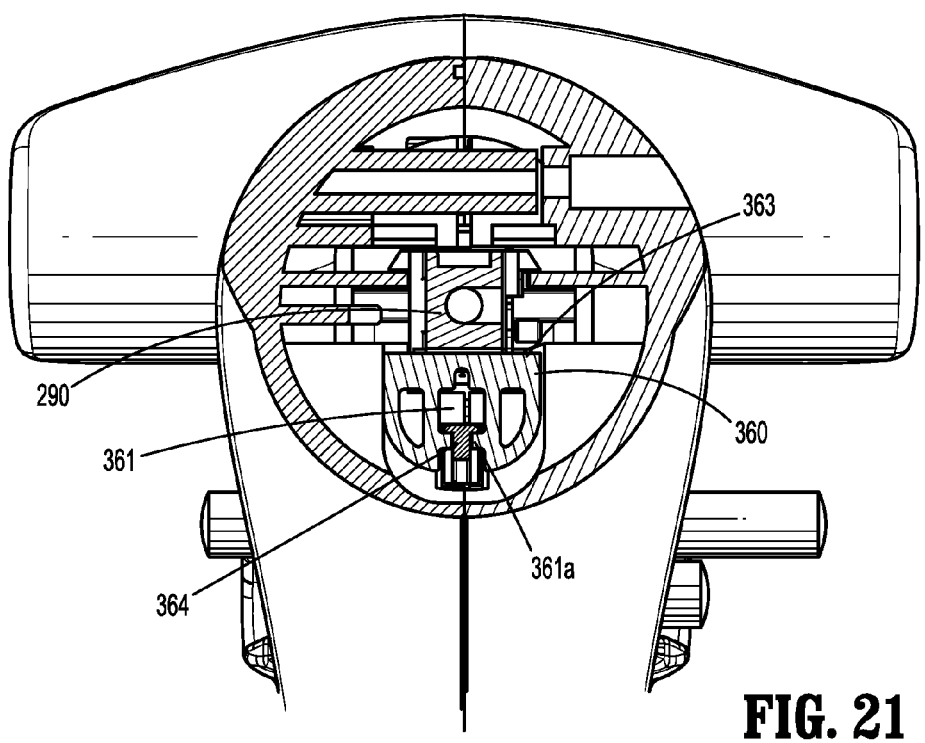
FIG. 21 is a front cross-sectional view taken along the section lines 21-21 of FIG. 20.

Locking assembly 260 has a first, a second, and a third position. In the first position illustrated in FIGS. 20 and 21, camming protrusion 361a (FIG. 18) of lock pawl 360 is positioned within distal recess 365 of disconnect link 364 permitting lock pawl 360 to engage actuation shaft 290. In the second position illustrated in FIGS. 23 and 24, camming protrusion 361a engages disconnect cam 366 moving lock pawl 360 against lock pawl biasing member 362 and away from actuation shaft 290. In the third position illustrated in FIG. 25, camming protrusion 361a of lock pawl 360 is positioned within proximal recess 367 permitting lock pawl 360 to engage actuation shaft 290.

Figure 19:
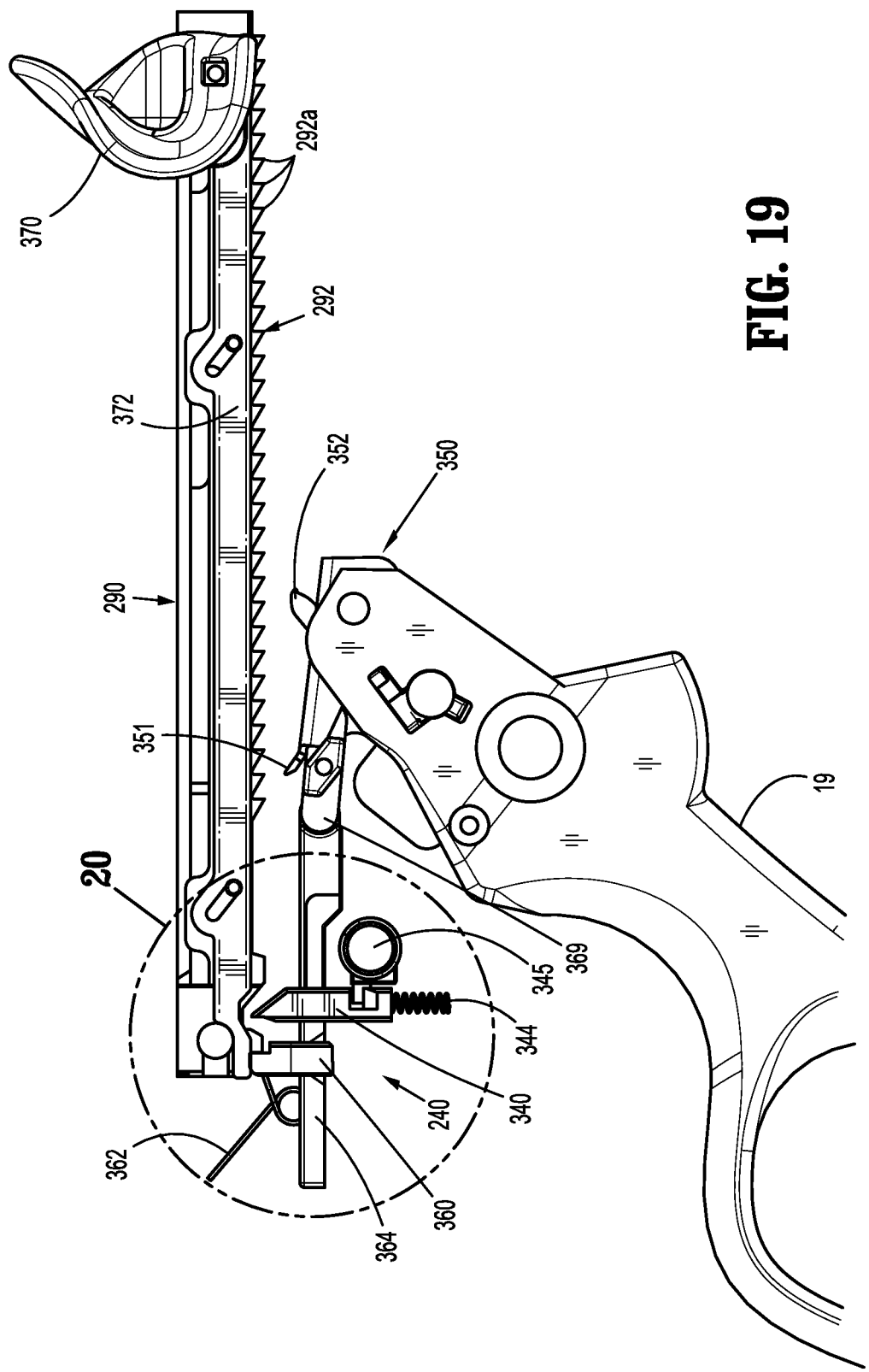
FIG. 19 is a side view of the internal components of the device of FIG. 14 in the initial condition.

Device 210 has an initial condition similar to device 10 wherein moveable handle 219 has not been compressed, the tool assembly is open, and the assemblies 240, 250, 260, 270 of device 210 are in their biased positions. More specifically, in the initial condition shown in FIGS. 19-21, locking assembly 260 is in the first position with lock pawl 360 engaging distal surface 294 of actuation shaft 290 such that actuation shaft 290 of device 210 is in its retracted position and is prevented from moving distally. Switch 345 is in the neutral position such that switch pawl 340 is received within a distal cutout 295 of actuation shaft 290. Switch pawl 340 may be positioned in distal cutout 295 to prevent proximal retraction of actuation shaft 290. In embodiments, actuation shaft 290 may include a shaft biasing member (not shown) which is positioned to urge actuation shaft 290 proximally but which is not strong enough to overcome the frictional forces of actuation shaft 290 and, thus, will not fully retract the actuation shaft 290 without manual assistance.

Figure 24:
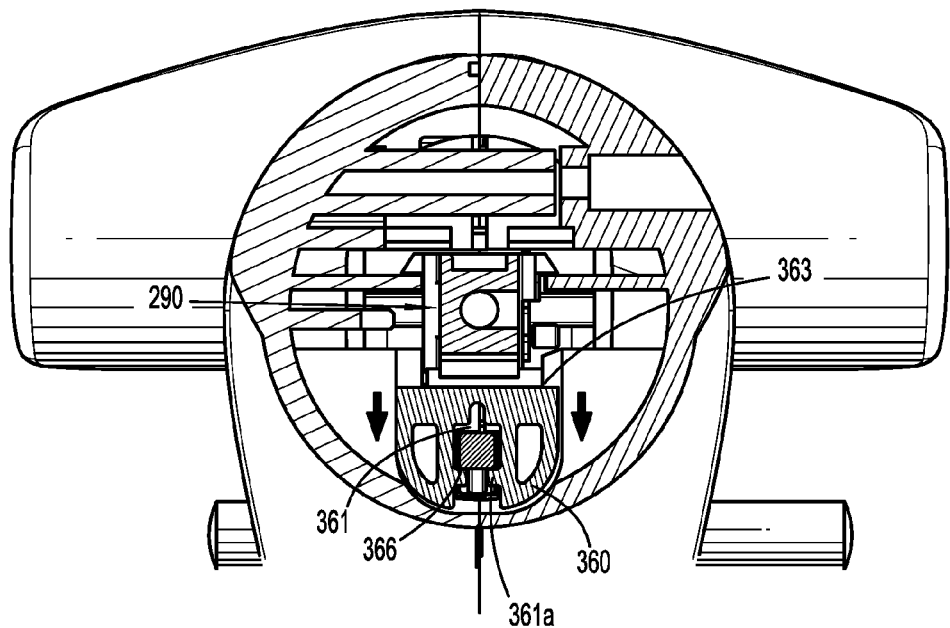
FIG. 24 is a front cross-sectional view taken along the section lines 24-24 of FIG. 23.
Figure 25:
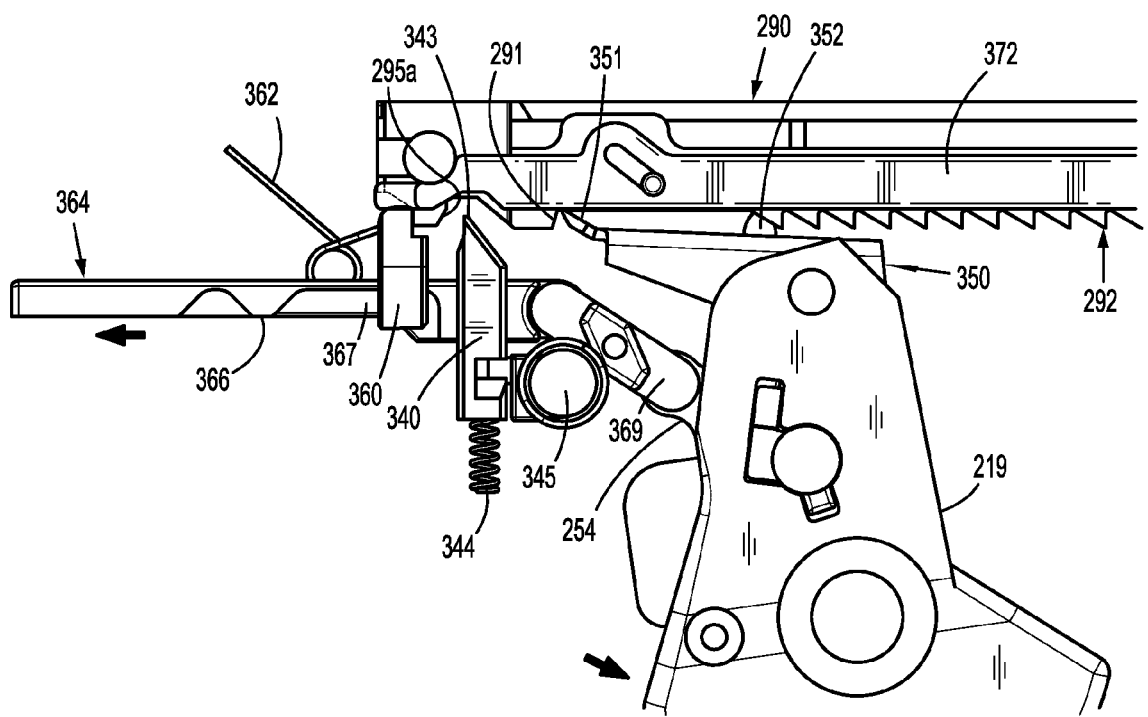
FIG. 25 is a side view of the internal components of the device of FIG. 14 in the grasping mode.
Figure 26:
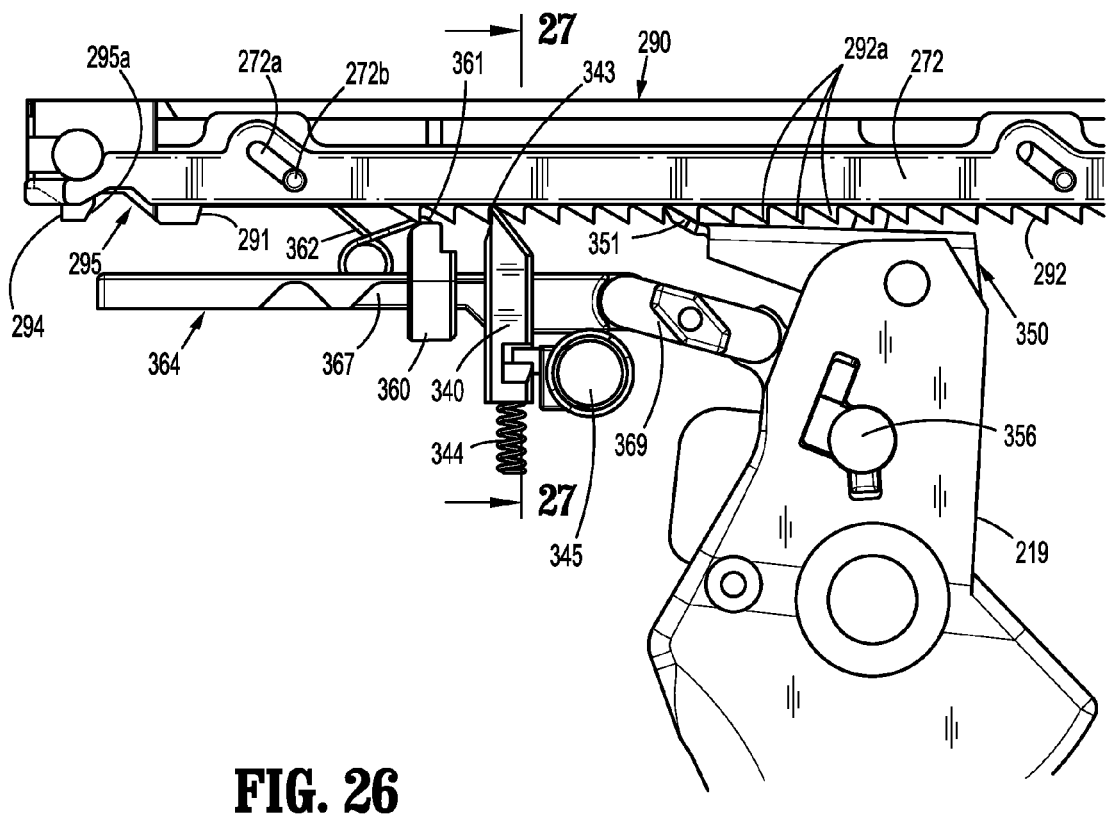
FIG. 26 is a side view of the internal components of the device of FIG. 14 in the clamping or firing mode.

In grasping mode, moveable handle 219 is compressed from a non-compressed position towards stationary handle 218 as shown in FIG. 23 with switch 345 depressed to move switch 345 from the neutral position to the depressed position against switch pawl biasing member 344 to permit retraction of actuation shaft 290. More specifically, as moveable handle 219 is compressed, boss 259 of moveable handle 219 advances disconnect link 364 by pivoting proximal link 369. As disconnect link 364 advances, locking assembly 260 transitions from its first position, past the second position, to the third position. When in the second position, camming protrusion 361a of lock pawl 360 engages proximal recess 367 of disconnect link 364 to urge lock pawl 360 out of engagement with distal surface 294 as shown in FIGS. 23 and 24. In the third position, camming protrusion 361a of lock pawl 360 engages proximal recess 367 and lock pawl 360 engages distal surface 294 as shown in FIG. 25. In embodiments, actuation shaft 290 is prevented from advancement when locking assembly 260 is in the second position by the shaft biasing member. In some embodiments, lock pawl camming surface 361 engages distal surface 94 of actuation shaft 290 to urge actuation shaft 290 proximally to prevent finger 351 from engaging a toothed rack 292 of actuation shaft 290.

In grasping mode, camming protrusion 361a of lock pawl 360 remains within proximal recess 367 and additional compression of moveable handle 219 urges a finger 351 of an actuation pawl 350 into engagement with a shoulder 291 of actuation shaft 290 to advance actuation shaft 290 and a grasping pawl 352 is received within a grasping slot 296 of actuation shaft 290 as discussed above with respect to device 10. In grasping mode, device 210 functions substantially similar to device 10. More specifically, as moveable handle 219 is moved away from stationary handle 218, actuation shaft 290 is retracted such that tool assembly 225 moves towards the open position and as moveable handle 219 is moved towards stationary handle 218, actuation shaft 290 is advanced such that tool assembly 225 moves towards the closed position. In embodiments, in the grasping mode both switch pawl 340 and lock pawl 360 are positioned distal to distal surface 294 of actuation shaft 290.

Figure 28:
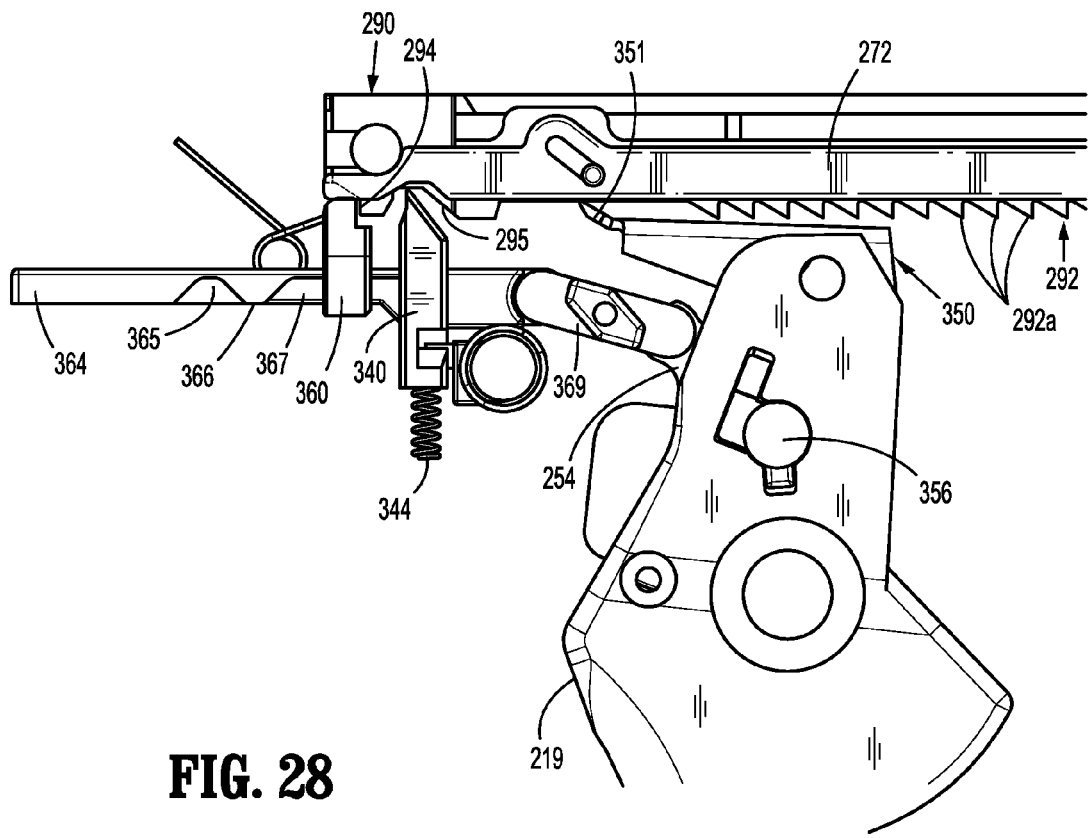
FIG. 28 is a side view of the internal components of the device of FIG. 14 between the grasping mode and the clamping mode.
Figure 29:
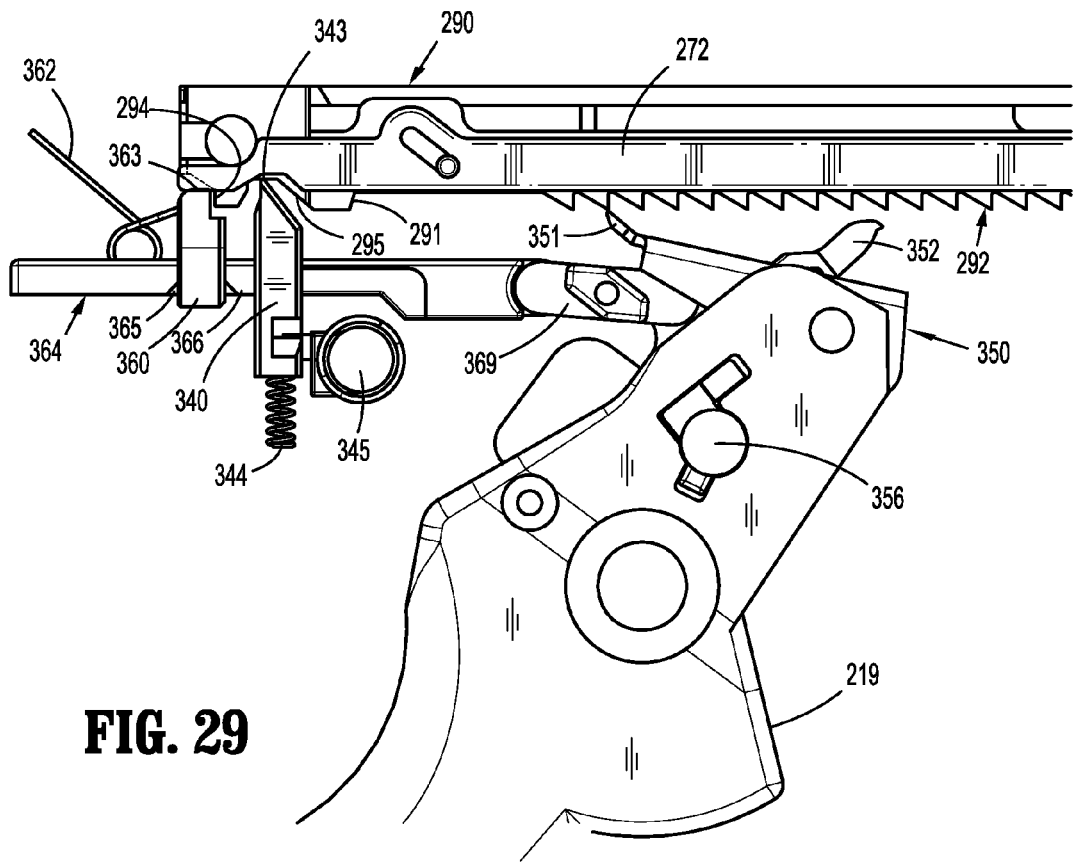
FIG. 29 is a side view of the internal components of the device of FIG. 14 in the clamping mode, with the device clamped.

To transition device 210 from the grasping mode to the clamping mode, switch 345 is returned to the neutral position such that switch pawl 340 engages distal cutout 295 of actuation shaft 290. In embodiments, the clinician must depress second end 348b or pull first end 348a to release switch 345 from wall 341a and return switch 345 to the neutral position. As actuation shaft 290 is advanced distally with switch 345 in the neutral position, camming surface 343 of switch pawl 340 engages surface features of actuation shaft 290 camming switch pawl 340 against switch pawl biasing member 344 as shown in FIG. 28. Actuation shaft 290 distally advances until lock pawl 360 engages distal surface 294. In some embodiments, an actuation button 356 is depressed to an off-centered position to retract grasping pawl 352 from grasping slot 296, similar to the retraction of grasping pawl 152 described above with respect to device 10, and moveable handle 219 is returned to the non-compressed position as illustrated in FIG. 29. As moveable handle 219 is returned to the non-compressed position, boss 259 retracts disconnect link 364 to return locking assembly 260 to the first position. As moveable handle 219 is compressed from the non-compressed position towards stationary handle 218, boss 259 transitions locking assembly 260 from the first position to the second position. When locking assembly 260 is in the second position, finger 251 engages toothed rack 292 of actuation shaft 290 to advance actuation shaft 290. Additional compression of moveable handle 219 advances disconnect link 294 to transition locking assembly 260 from the second position to the third position. As actuation shaft 290 advances lock pawl camming surface 361 of lock pawl 360 and camming surface 343 of switch pawl 340 engage surface features of actuation shaft 290, including teeth 292a of toothed rack 292, camming lock pawl 360 and switch pawl 340 against lock pawl biasing member 362 and switch pawl biasing member 344 respectively. In clamping mode, switch pawl 340 engages teeth 292a of toothed rack 292 to prevent actuation shaft 290 from retraction and tool assembly 225 is locked in the closed or clamped position. Similar to device 10 described above, continued cycling of movable handle 219 fires staples from a cartridge assembly (not shown).

Refraction assembly 270 functions substantially identical to retraction assembly 70 of device 10 as discussed above. When retraction plate 372 is moved below toothed rack 292, retraction plate 372 engages switch pawl 340, actuation pawl 350, and locking pawl 360 preventing each pawl from engaging actuation shaft 290 permitting proximal retraction of actuation shaft 290 and returning device 210 to the initial condition.

Device 210 is capable of being in clamping mode without transitioning to grasping mode by maintaining switch 345 in the neutral position and cycling moveable handle 219. As moveable handle 219 is compressed towards stationary handle 218, finger 351 engages toothed rack 92 while lock pawl assembly 260 is in the second position as described above.

Figure 30:
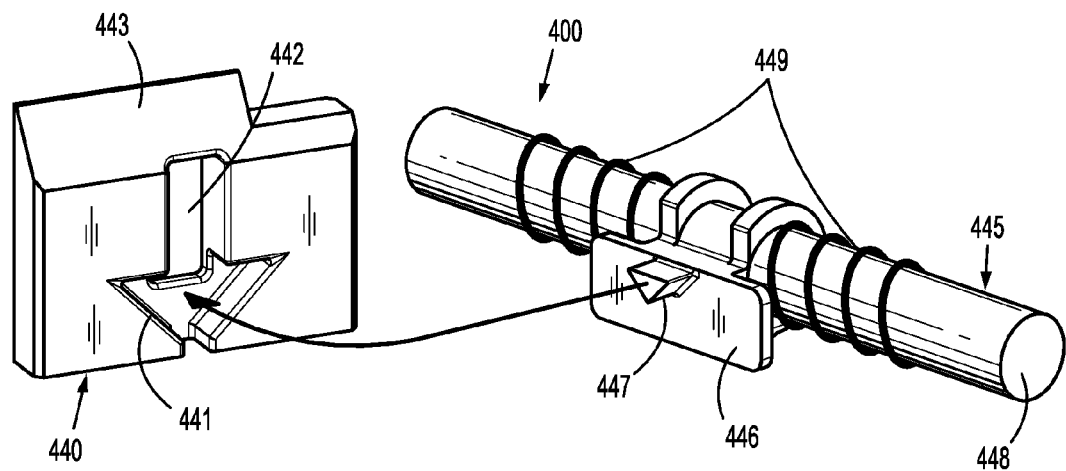
FIG. 30 is perspective view of another embodiment of a presently disclosed switch assembly.
Figure 31:
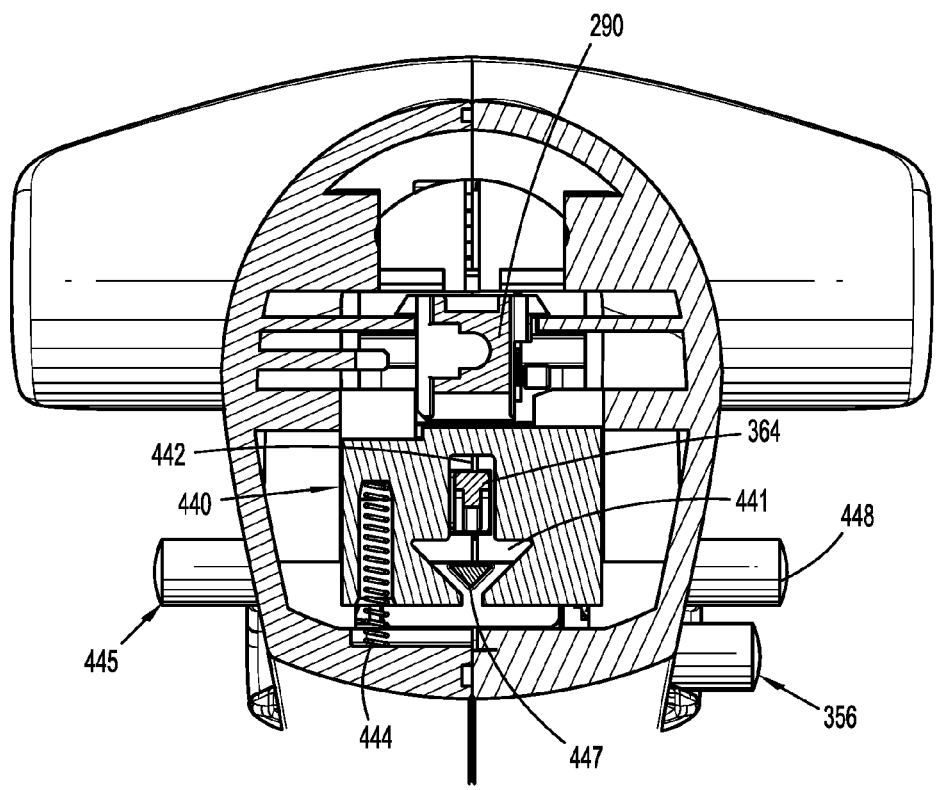
FIG. 31 is a front cross-sectional view of the switch assembly of FIG. 30 illustrating the switch in a neutral position.
Figure 32:
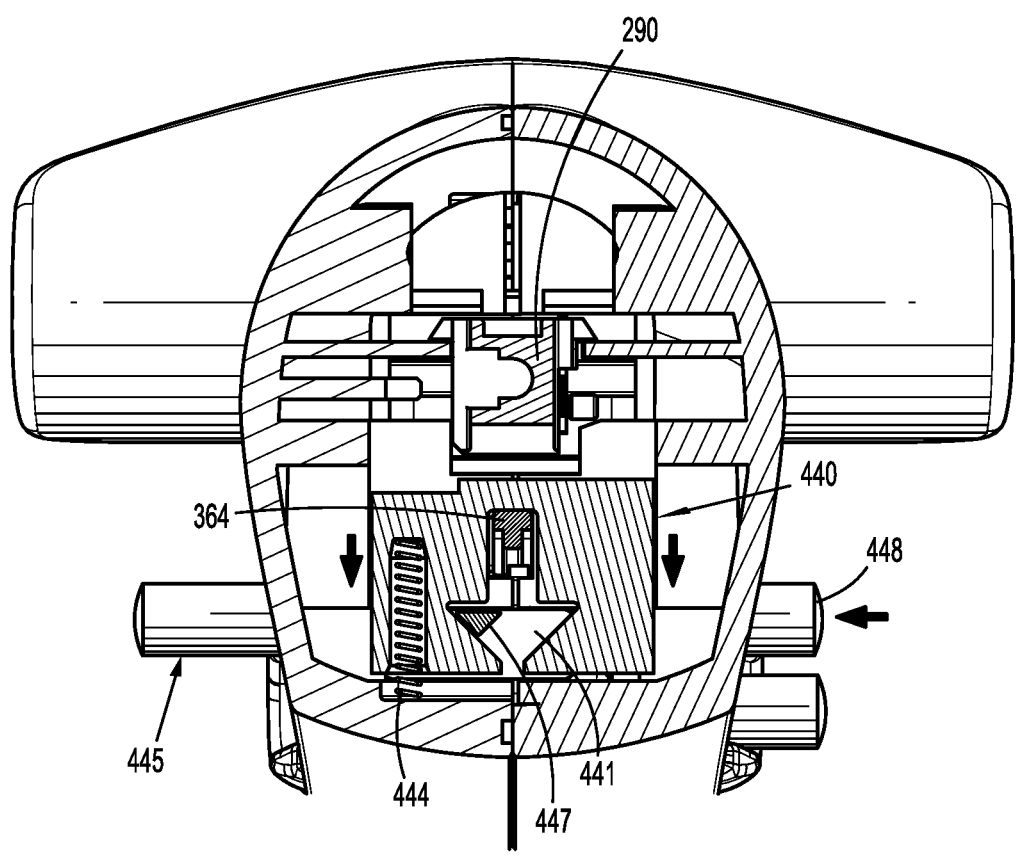
FIG. 32 is a front cross-sectional view of the switch assembly of FIG. 30 illustrating the switch in a depressed position.

FIGS. 30-32 illustrate switch assembly 400 as an alternative embodiment of the presently disclosed switch assembly 300 for use with device 210. Switch assembly 400 is substantially similar to switch assembly 100 described above with respect to device 10 and functions in a substantially similar manner to switch assembly 300. Accordingly, only the differences with be discussed in detail below.

With reference to FIG. 30, switch assembly 400 includes a switch pawl 440, a switch pawl biasing member 444 (FIG. 31), and a switch 445. Switch pawl 440 includes a detent receiving slot 441 in a proximally facing surface and a camming surface 443. Similar to switch pawl 340, disconnect cam 367 may pass through a neutral slot 442 in switch pawl 440. Switch 445 is generally cylindrical and includes a raised portion 446, a detent 447, ends 448, and switch biasing members 449. Switch 445 has a neutral position (FIG. 31) and a depressed position (FIG. 32) similar to switch 145. As can be appreciated, either end 448 of switch 445 may be depressed to transition switch 445 from the neutral position to the depressed position.

According to aspects of this disclosure, a method for using a surgical stapling device is disclosed. The method includes providing a surgical stapling device, and clamping tissue within a tool assembly of the surgical stapling device. The surgical stapling device provided in the method may include any of the surgical stapling devices 10, 210 and switch assemblies 100, 300, 400 disclosed herein.

The method may include the step of manipulating the tissue with the tool assembly before the step of clamping. Manipulating may include grasping, repositioning, or severing the tissue.

The method may also include the step of firing staples through the tissue after the step of clamping. The step of firing may include firing a selected number of staple from a staple cartridge or firing all of the staples from the staple cartridge.

The method may further include the step of releasing the tissue after the step of clamping. The step of releasing may include proximally retracting a refraction handle of the surgical stapling device.

It will be understood that various modifications may be made to the embodiments disclosed herein. For example, it is envisioned that the surgical stapling device disclosed may be used in association with other surgical devices, e.g., clip appliers, dissectors, electrosurgical scaling devices, etc. Further, the device may also include tool assemblies other than staplers or those devices which eject a fastener, e.g., sealing devices (electrosurgical and non-electrosurgical), etc. The button or other actuator for changing the mode of operation for the device may be provided on one side or both sides of the handle assembly. Therefore, the above description should not be construed as limiting, but merely as exemplifications of preferred embodiments. Those skilled in the art will envision other modifications within the scope and spirit of the claims appended hereto.

What is claimed is:

1. A surgical device comprising:
a handle assembly including an actuation shaft, a stationary handle, and a movable handle, the movable handle being moveable from a non-compressed position to a compressed position and being operably associated with the actuation shaft such that movement of the movable handle effects axial movement of the actuation shaft between an extended position and a retracted position;
an elongated member extending distally from the handle assembly, the elongated member defining a longitudinal axis;
a tool assembly supported on a distal end of the elongated member, the tool assembly including a cartridge assembly having a plurality of staples supported therein and an anvil assembly, the anvil assembly and the cartridge assembly being movable in relation to each other between open and closed positions;
an actuation assembly including an actuation pawl pivotally coupled to the moveable handle and operatively associated with the actuation shaft to advance the actuation shaft upon movement of the moveable handle, the actuation assembly further including an actuation arm, an actuation button movable between a centered position and a non-centered position, and a grasping pawl coupled to an end of the actuation arm, the actuation arm moveable between an extended position when the actuation button is in the centered position and a retracted position when the actuation button is in the off-centered position, wherein in the extended position the grasping pawl is positioned to engage the actuation shaft in a grasping mode of operation and in the retracted position the grasping pawl is out of engagement with the actuation shaft in a clamping mode of operation; and a mode selection mechanism including a lock pawl and a lock pawl biasing member positioned to urge the lock pawl into engagement with a distal surface of the actuation shaft to prevent advancement of the actuation shaft from the retracted position, the mode selection mechanism further including a switch pawl, a switch, and a switch pawl biasing member that urges the switch pawl into engagement with the actuation shaft, the switch configured to cam the switch pawl against the switch pawl biasing member and out of engagement with the actuation shaft to permit operation of the device in the grasping mode of operation.

2. The device of claim 1, wherein compression of the moveable handle towards the stationary handle effects advancement of the actuation shaft and when in the grasping mode of operation movement of the movable handle away from the stationary handle effects retraction of the actuation shaft.

3. The device of claim 1, wherein the switch is biased in a neutral position.

4. The device of claim 1, wherein the switch pawl prevents retraction of the actuation shaft when the switch pawl is engaged with the actuation shaft.

5. The device of claim 1, wherein the switch includes a detent operatively associated with the switch pawl and configured to cam the switch pawl against the switch pawl biasing member and out of engagement with the actuation shaft.

6. The device of claim 1, wherein the mode selection mechanism includes a disconnect link operatively associated with the moveable handle and the lock pawl, the disconnect link configured to cam the lock pawl against the lock pawl biasing member and out of engagement with the actuation shaft.

7. The device of claim 6, wherein the disconnect link has a distal recess and the lock pawl has a camming protrusion, the camming protrusion being disposed in the distal recess when the device is in the grasping mode of operation.

8. The device of claim 7, wherein the disconnect link has a proximal recess, the lock pawl engaging the distal surface of the actuation shaft when the camming protrusion is disposed in the proximal recess.

* * * * *